(12) United States Patent
Peyman

(10) Patent No.: US 11,433,260 B2
(45) Date of Patent: *Sep. 6, 2022

(54) CANCER TREATMENT METHODS USING THERMOTHERAPY AND/OR ENHANCED IMMUNOTHERAPY

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 819 days.

This patent is subject to a terminal disclaimer.

(21) Appl. No.: 16/200,195

(22) Filed: Nov. 26, 2018

(65) Prior Publication Data

US 2019/0091350 A1 Mar. 28, 2019

Related U.S. Application Data

(63) Continuation-in-part of application No. PCT/US2018/054880, filed on Oct. 8, 2018, and a
(Continued)

(51) Int. Cl.
*A61N 7/02* (2006.01)
*A61K 49/22* (2006.01)
(Continued)

(52) U.S. Cl.
CPC .............. *A61N 7/02* (2013.01); *A61B 5/0036* (2018.08); *A61B 5/0093* (2013.01);
(Continued)

(58) Field of Classification Search
CPC ... A61B 5/0036; A61B 5/0093; A61B 5/0095; A61B 5/015; A61B 8/085; A61B 8/13;
(Continued)

(56) References Cited

U.S. PATENT DOCUMENTS 3,993,754 A 11/1976 Rahman et al.
4,235,871 A 11/1980 Papahadjopoulos et al.
(Continued)

OTHER PUBLICATIONS

Xin et al. "Clinical applications of low-intensity pulsed ultrasound and its potential role in urology." Transl Androl Urol. Apr. 2016; 5(2): 255-266.*
(Continued)

*Primary Examiner* — Amanda Lauritzen Moher
(74) *Attorney, Agent, or Firm* — The Law Office of Patrick F. O'Reilly III, LLC

(57) ABSTRACT

Cancer treatment methods using thermotherapy and/or enhanced immunotherapy are disclosed herein. In one embodiment, the method comprising the steps of administering a plurality of nanoparticles to target a tumor in a patient, the nanoparticles being coated with an antitumor antibody, cell penetrating peptides (CPPs), and a polymer, and the nanoparticles containing medication and/or gene, and a dye or indicator in the polymer coating, at least some of the nanoparticles attaching to surface antigens of tumor cells so as to form a tumor cell/nanoparticle complex; exciting the nanoparticles using an ultrasound source generating an ultrasonic wave so as to peel off the polymer coating of the nanoparticles, thereby releasing the dye or indicator into the circulation of the patient and the medication and/or gene at the tumor site; and imaging a body region of the patient so as to detect the dye or indicator released into the circulation of the patient.

13 Claims, 5 Drawing Sheets

Related U.S. Application Data continuation-in-part of application No. 14/976,321, filed on Dec. 21, 2015, now Pat. No. 10,136,820.

(60) Provisional application No. 62/720,258, filed on Aug. 21, 2018, provisional application No. 62/614,456, filed on Jan. 7, 2018, provisional application No. 62/577,485, filed on Oct. 26, 2017, provisional application No. 62/569,592, filed on Oct. 8, 2017.

(51) Int. Cl.

| | |
|---|---|
| A61N 2/00 | (2006.01) |
| A61B 5/00 | (2006.01) |
| A61M 1/38 | (2006.01) |
| A61K 41/00 | (2020.01) |
| A61K 47/69 | (2017.01) |
| A61K 9/00 | (2006.01) |
| A61B 8/08 | (2006.01) |
| A61K 9/127 | (2006.01) |
| A61K 49/00 | (2006.01) |
| A61N 7/00 | (2006.01) |
| A61B 5/01 | (2006.01) |
| A61K 45/06 | (2006.01) |
| A61N 1/40 | (2006.01) |
| A61B 8/13 | (2006.01) |
| A61N 1/36 | (2006.01) |
| A61N 1/32 | (2006.01) |

(52) U.S. Cl.
CPC .......... *A61B 5/0095* (2013.01); *A61B 5/015* (2013.01); *A61B 8/085* (2013.01); *A61B 8/481* (2013.01); *A61K 9/0019* (2013.01); *A61K 9/0043* (2013.01); *A61K 9/127* (2013.01); *A61K 41/0028* (2013.01); *A61K 41/0052* (2013.01); *A61K 45/06* (2013.01); *A61K 47/6913* (2017.08); *A61K 47/6929* (2017.08); *A61K 49/0043* (2013.01); *A61K 49/22* (2013.01); *A61K 49/221* (2013.01); *A61K 49/222* (2013.01); *A61K 49/227* (2013.01); *A61M 1/38* (2013.01); *A61N 2/004* (2013.01); *A61N 7/00* (2013.01); *A61B 8/13* (2013.01); *A61N 1/327* (2013.01); *A61N 1/36002* (2017.08); *A61N 1/406* (2013.01); *A61N 2007/0052* (2013.01); *A61N 2007/0073* (2013.01); *A61N 2007/0078* (2013.01); *A61N 2007/0095* (2013.01)

(58) Field of Classification Search
CPC ............... A61B 8/481; A61K 41/0028; A61K 41/0052; A61K 45/06; A61K 47/6913; A61K 47/6929; A61K 49/0043; A61K 49/22; A61K 49/221; A61K 49/222; A61K 49/227; A61K 9/0019; A61K 9/0043; A61K 9/127; A61M 1/38; A61N 1/327; A61N 1/36002; A61N 1/406; A61N 2/004; A61N 2007/0052; A61N 2007/0073; A61N 2007/0078; A61N 2007/0095; A61N 7/00; A61N 7/02
See application file for complete search history.

(56) References Cited

U.S. PATENT DOCUMENTS

| | | | |
|---|---|---|---|
| 4,522,803 A | 6/1985 | Lenk et al. | |
| 4,586,512 A | 5/1986 | Do-huu et al. | |
| 4,620,546 A | 11/1986 | Aida et al. | |
| 4,658,828 A | 4/1987 | Dory | |
| 4,891,043 A | 1/1990 | Zeimer et al. | |
| 5,094,854 A | 3/1992 | Ogawa et al. | |
| 5,118,666 A | 6/1992 | Habener | |
| 5,149,319 A | 9/1992 | Unger | |
| 5,203,782 A | 4/1993 | Gudov et al. | |
| 5,220,181 A | 6/1993 | Kanal et al. | |
| 5,545,618 A | 8/1996 | Buckley et al. | |
| 5,935,942 A | 8/1999 | Zeimer | |
| 5,976,502 A | 11/1999 | Khoobehi et al. | |
| 6,179,767 B1 | 1/2001 | Ziegler et al. | |
| 6,197,022 B1 | 3/2001 | Baker | |
| 6,248,727 B1 | 6/2001 | Zeimer | |
| 6,552,053 B2 | 4/2003 | Sun et al. | |
| 6,566,595 B2 | 5/2003 | Suzuki et al. | |
| 6,583,111 B1 | 6/2003 | DiMarchi et al. | |
| 6,641,553 B1 | 11/2003 | Chee et al. | |
| 6,984,655 B1 | 1/2006 | Mori et al. | |
| 7,638,139 B2 | 12/2009 | Peyman | |
| 8,324,344 B2 | 12/2012 | Kisiel | |
| 8,481,082 B2* | 7/2013 | Peyman ............ A61K 41/0052 424/489 |
| 8,808,268 B2 | 8/2014 | Peyman | |
| 2002/0174743 A1 | 11/2002 | Mukherjee et al. | |
| 2003/0014089 A1 | 1/2003 | Chow et al. | |
| 2003/0022374 A1 | 1/2003 | Greenbaum et al. | |
| 2003/0119033 A1 | 6/2003 | Mikolajczyk et al. | |
| 2004/0003839 A1 | 1/2004 | Curtain | |
| 2005/0004625 A1 | 1/2005 | Chow | |
| 2006/0173362 A1 | 8/2006 | Toms et al. | |
| 2008/0260745 A1 | 10/2008 | Ponniah et al. | |
| 2009/0156932 A1 | 6/2009 | Zharov | |
| 2010/0185260 A1 | 7/2010 | Olson | |
| 2010/0211146 A1 | 8/2010 | Strowbridge et al. | |
| 2010/0303716 A1* | 12/2010 | Jin .................... A61M 37/0092 424/1.11 |
| 2011/0270153 A1 | 11/2011 | Olson | |
| 2011/0287035 A1 | 11/2011 | Peyman | |
| 2012/0226139 A1 | 9/2012 | Peyman | |
| 2015/0202466 A1 | 7/2015 | Gertner | |
| 2016/0022976 A1 | 1/2016 | Peyman | |
| 2016/0129131 A1 | 5/2016 | Vitari et al. | |
| 2016/0129133 A1 | 5/2016 | McCreedy et al. | |
| 2016/0186147 A1 | 6/2016 | Cady et al. | |
| 2016/0296175 A1* | 10/2016 | Liu ........................ G01K 7/36 |
| 2022/0096873 A1* | 3/2022 | Peyman .................. A61N 5/067 |

OTHER PUBLICATIONS

Kruse et al. "Spatial and Temporal Controlled Tissue Heating on a Modified Clinical Ultrasound Scanner for Generating Mild Hyperthermia in Tumors." IEEE Trans Biomed Eng. Jan. 2010; 57(1): 155-166.*

Mossman "Quantum dots track who gets into cell nucleus" Physorg.com, Sep. 2, 2010, available at http://www.physorg.com/news202628740.html.

Wang et al. Nucleic Acid Conjugated Nanomaterials for Enhanced Molecular Recognition. ACS Nano 3 (2009) 2451-2460.

You et al. "Incorporation of quantum dots on virus in polycationic solution" Int. J. Nanomedicine, vol. 1, No. 1 (2006), pp. 59-64.

Anscombe "Quantum Dots: Small Structures Poised to Break Big" Photonics Spectra, Jul. 2005, pp. 94-96.

Mali et al. "Intravitreous Injection of a Membrane Depolarization Agent Causes Retinal Degeneration Via Matrix Metalloproteinase-9" Investigative Ophthalmology and Visual Science, vol. 46, No. 6 (2005), pp. 2125-2132.

Greenbaum et al. "Application of Photosynthesis to Artificial Sight" paper presented at the Nanoscale Science and Technology in Medicine Symposium, 23rd International Conference of the IEEE Engineering in Medicine and Biology Society, Oct. 25-28, 2001, Istanbul, Turkey, vol. 4, pp. 4089-4091.

Aylott "Optical nanosensors-an enabling technology for intracellular measurements" Analyst, vol. 128 (2003), pp. 309-312.

Buck et al. "Optochemical nanosensor PEBBLEs: photonic explorers for bioanalysis with biologically localized embedding" Current Opinion in Chemical Biology, vol. 8 (2004), pp. 540-546.

Fehr et al. "Development and use of fluorescent nanosensors for metabolite imaging in living cells" Biochemical Society Transactions, vol. 23, part 1 (2005), pp. 287-290.

(56) References Cited

OTHER PUBLICATIONS

Ferreira et al. "Downstream processing of plasmid DNA for gene therapy and DNA vaccine applications," Tibtech, vol. 18 (2000), pp. 380-387.
Fei et al. "Glucose nanosensors based on redox polymer/glucose oxidase modified carbon fiber nanoelectrodes" Talanta, vol. 65 (2005), pp. 918-924.
Haes et al. "A unified view of propagating and localized surface plasmon resonance biosensors" Anal. Bioanal. Chem, vol. 379 (2004), pp. 920-930.
Cullum et al. "The development of optical nanosensors for biological measurements" Tibtech, vol. 18 (2000), pp. 388-393.
Hauser and Zhang, "Peptides as biological semiconductors," Nature, vol. 468 (2010), p. 516.
Audero et al. Sporadic Autonomic Dysregulation and Death Associated with Excessive Serotonin Autoinhibition. Science, vol. 321 (2008), pp. 130-133.
De Crespigny et al. Magnetic Resonance Imaging Assessment of Cerebral Hemodynamics During Spreading Depression in Rats. Journal of Cerebral Blood Flow and Metabolism, vol. 18 (1998), pp. 1008-1017.
Hohne et al. Acetazolamide prevents hypoxic pulmonary vasoconstriction in conscious dogs. J. Appl. Physiol. vol. 97 (2004), pp. 515-521.
Rio-Portilla et al. REM Sleep Post-Eye Movement Activation. International Journal of Bioelectromagnetism, vol. 10, No. 4 (2008), pp. 192-208.
IBM Press Release, Made in IBM Labs: IBM Scientists Demonstrate World's Fastest Graphene Transistor, Feb. 5, 2010, 1 page.
Kurzwiel AI, Engineers envision 2-dimensional graphene metamaterials and 1-atom-thick optical devices. Jun. 10, 2011, 1 page; internet address: http://www.kurzweilai.net/engineers-envision-2-dimensional-graphene-metamaterials-and-1-atom-thick-optical-devices.
Erogbogbo et al. Plasmonic gold and luminescent silicon nanoplatforms for multimode imaging of cancer cells. Integr. Biol. 5 (2013) 144-150.
Yezhelyev et al., Proton-Sponge-Coated Quantum Dots for siRNA Delivery and Intracellular Imaging. J Am. Chem. Soc. 130 (2008) 9006-9012.
Rajan and Raj. Potential Drug Delivery Applications of Chitosan Based Nanomaterials. I.Re.CH.E. 5 (2013) 145-155.
Song et al., Tumor Cell Targeting Using Folate-Conjugated Fluorescent Quantum Dots and Receptor-Mediated Endocytosis. Clinical Chemistry 55 (2009) 955-963.
Liu et al. Bioconjugated Pluronic Triblock-Copolymer Micelle-Encapsulated Quantum Dots for Targeted Imaging of Cancer: In Vitro and In Vivo Studies. Theranostics 2 (2012) 705-713.
Jin et al. Preparation and Characterization of Highly Fluorescent, Glutathione-coated Infrared Quantum Dots for in Vivo Fluorescence Imaging. Int. J. Mol. Sci. 9 (2008) 20440-2061.
Liu et al., Endocytic Trafficking of Nanoparticles Delivered by Cell-penetrating Peptides Comprised of Nona-arginine and a Penetration Accelerating Sequence, PLOS One 8 (2013) e67100, 12 pages.
Liu et al., Intracellular Delivery of Nanoparticles and DNAs by IR9 Cell-penetrating Peptides, PLOS One 8 (2013) e64205 (13 pages).
Liu et al., Cell-Penetrating Peptide-Functionalized Quantum Dots for Intracellular Delivery. J. Nanosci. Nanotechnol. 10 (2010) 7897-7905.
Liu et al., Cellular Internalization of Quantum Dots Noncovalentiy Conjugated with Arginine-Rich Cell-Penetrating Peptides. J. Nanosci. Nanotechnol. 10 (2010) 6534-6543.
Xu et al., Nona-Arginine Facilitates Delivery of Quantum Dots into Cells via Multiple Pathways. J. Biomedicine and Biotechnology 2010, Article ID 948543, 11 pages.
Delehanty et al., Self-Assembled Quantum Dot-Peptide Bioconjugates for Selective Intracellular Delivery. Bioconjug Chem 17 (2006) 920-927.
Ho et al., Combining QD-FRET and Microfluidics to Monitor DNA Nanocomplex Self-Assembly in Real-Time. J. Vis Exp. 30 (2009) 1432, 3 pages.
Biju et al., Delivering quantum dots to cells: bioconjugated quantum dots for targeted and nonspecific extracellular and intracellular imaging. Chem. Soc. Rev 39 (2010) 3031-3056.
Algar and Krull. Toward A Multiplexed Solid-Phase Nucleic Acid Hybridization Assay Using Quantum Dots as Donors in Fluorescence Resonance Energy Transfer. Anal Chem. 81 (2009) 4113-4120.
Gao et al. In vivo cancer targeting and imaging with semiconductor quantum dots. Nature Biotechnology 22 (2004) 969-976.
Gussin et al. Binding of Muscimol-Conjugated Quantum Dots to GabaC Receptors. J. Am Chem. Soc. 128 (2006) 15701-15713.
He et al. Highly Luminescent Water-Dispersible Silicon Nanowires for Long Term Immunofluorescent Cellular Imaging. Angew. Chem. Int. Ed. 50 (2011) 3080-3083.
Heiss et al. Image-guided convection-enhanced delivery of muscimol to the primate brain. J Neurosurg. 112 (2010) 790-795.
Lugo et al. Remote switching of cellular activity and cell signaling using light in conjunction with quantum dots. Biomedical Optics Express 3. (2012) 447-454.
Pappas et al. Nanoscale Engineering of a Cellular Interface with Semiconductor Nanoparticle Films for Photoelectric Stimulation of Neurons. Nano Letters 7 (2007) 513-519.
Rosenthal et al. Biocompatible Quantum Dots for Biological Applications. Chem Biol. 18 (2011) 10-24.
Templeton. Tiny Q-dots may enable more precise brain surgery. Pittsburgh Post—Gazette, Apr. 10, 2007, 4 pages.
van Rooy et al. Comparison of five different targeting ligands to enhance accumulation of liposomes into the brain. Journal of Controlled Release 150 (2011) 30-36.
Wen et al. Theranostic liposomes loaded with quantum dots and apomorphine for brain targeting and bioimaging. International Journal of Nanomedicine 7 (2012) 1599-1611.
Zhong et al. Modular design of an ultrahigh-intensity nanoparticle probe for cancer cell imaging and rapid visual detection of nucleic acids. Chem Commun., 48 (2012) 6277-6279.
Baker and Baker. Luminescent Carbon Nanodots: Emergent Nanolights. Angew. Chem. Int. Ed. 49 (2010) 6726-6744.
Hofmann-Amtenbrink et al. Superparamagnetic nanoparticles for biomedical applications, Nanostructured Materials for Biomedical Applications, (ed. M.C. Tan.) 2009, chap. 5, 119-149.
Joeres et al. Quantitative Comparison of Optical Coherence Tomography after Pegaptanib or Bevacizumab in Neovascular Age-Related Macular Degeneration, Ophthalmology 115 (2008) 347-354.
Min et al. Lentivirus-Mediated sFlt-1 Gene Fragment Transfer Suppresses Retinal Neovascularization. Current Eye Research 34 (2009) 401-410.
Mulder et al. Quantum dots for multimodal molecular imaging of angiogenesis. Angiogenesis 13 (2010) 131-134.
Singerman. Combination therapy using the small interfering RNA bevasiranib. Retina 2009, Abstract Only.
Smith et al., Bioconjugated Quantum Dots for In Vivo Molecular and Cellular Imaging. Adv. Drug Deliv. Rev. 60 (2008) 1226-1240.
You et al. Incorporation of quantum dots on virus in polycationic solution. Int. J. Nanomedicine 1 (2006) 59-64.
Lee et al. The retinoblastoma susceptibility gene encodes a nuclear phosphoprotein associated with DNA binding activity. Nature, 329 (1987) 642-645.
Tomczak et al. Designer polymer-quantum dot architectures. Progress in Polymer Science, 34 (2009) 393-430.
Duan and Nle. Cell-penetrating quantum dots based on multivalent and endosome-disrupting surface coatings. J Am. Chem. Soc. 129 (2007) 3333-3338.
Kim and Taton. Multicomponent nanoparticles via self-assembly with cross-linked block copolymer surfactants. Langmuir, 23 (2007) 2198-2202.
Pan et al. Silica Cross-linked Micelles Loading with Silicon Nanoparticles: Preparation and Characterization. ACS Appl. Mater. Interfaces 5 (2013) 7042-7049.

(56) References Cited

OTHER PUBLICATIONS

Lv et al., Surface modification of quantum dots and magnetic nanoparticles with PEG-conjugated chitosan derivatives for biological applications. Chemical Papers 67 (2013) 1404-1413.
Suzuki et al. Quantum Dot FRET Biosensors that Respond to pH, to Proteolytic or Nucleolytic Cleavage, to DNA Synthesis, or to a Multiplexing Combination J. Am. Chem. Soc. 130 (2008) 5720-5725.
Huang et al. Intermolecular and Intramolecular Quencher Based Quantum Dot Nanoprobes for Multiplexed Detection of Endonuclease Activity and Inhibition, Anal. Chem. 83 (2011) 8913-8918.
Akbarzadeh et al. Liposome: classification, preparation, and applications. Nanoscale Research Letters 8:102 (2013) 1-9.
Sander et al. CRISPR-Cas systems for editing, regulating and targeting genomes. Nature Biotechnology 32:4 (2014) 347-355.
Peyman et al. A High-Resolution 3D Ultrasonic System for Rapid Evaluation of the Anterior and Posterior Segment. Ophthalmic Surgery, Lasers & Imaging 43 (2012) 143-151.
Andor Technology, "Transport Across the Nuclear Membrane Using Quantum Dots," Aug. 23, 2011, available at http://www.andor.com/company/news/?docID=1224.
Boyden, "Optogenetics: Using Light to Control the Brain," The Dana Foundation, Nov. 30, 2011, available at http://www.dana.org/news/cerebrum/detail.aspx?id=34614.
Buchen, "Illuminating the Brain," Nature, vol. 465, May 6, 2010, pp. 26-28.
Dixit et al., "Quantum Dot Encapsulation in Viral Capsids," Nano Letters, vol. 6, No. 9 (2006); pp. 1993-1999.
Deisseroth, "Optogenetics," Nature Methods, Published online Dec. 20, 2010, available at http://www.stanford.edu/group/dlab/papers/deisserothnature2010.pdf.
Deisseroth, "Optogenetics: Controlling the Brain with Light [Extended Version]," Scientific American, Published online Oct. 20, 2010, available at http://www scientificamerican.com/article.cfm?id=optogenetics-controlling.
Dubertret et al., "In vivo Imaging of Quantum Dots Encapsulated in Phospholipid Micelles," Science, vol. 298, No. 5599 (2002), pp. 1759-1762.
Gill et al., "Fluorescence Resonance Energy Transfer in CdSe/ZnS—DNA Conjugates: Probing Hybridization and DNA Cleavage," J. Phys. Chem. B., vol. 109 (2005), pp. 23175-23179.
Joo et al., "Enhanced Real-Time Monitoring of Adeno-Associated Virus Trafficking by Virus-Quantum Dot Conjugates," ACSNano, vol. 5, issue 5 (2011); pp. 3523-3535.
Michalet et al., "Quantum Dots for Live Cells, in Vivo Imaging, and Diagnostics," Science, 307, No. 5709 (2005), pp. 538-544.
Yizhar et al., "Optogenetics in Neural Systems," Neuron, vol. 71 (2011), 9-34.
Zhang et al., "Optogenetic interrogation of neural circuits: technology for probing mammalian brain structures," Nature Protocols, vol. 5, No. 3 (2010), pp. 439-456.
Aguilera et al. "Systemic in vivo distribution of activatable cell penetrating peptides is superior to cell penetrating peptides," Integr Biol (Camb), vol. 1 , No. 5-6 (2009), pp. 371-381.
Kelley. "What Clinicians Need to Know About Molecular Markers in Solid Tumors" Aug. 6, 2010, available at http://www.medscape.org/viewarticle/725989.
Nguyen et al. "Surgery with molecular fluorescence imaging using activatable cell-penetrating peptides decreases residual cancer and improves survival," Proc. Nat. Acad. Sci., 107 (2010) 4317-4322.
Olson et al. "In vivo characterization of activatable cell penetrating peptides for targeting protease activity in cancer," Integr Bioi, 1 (2009) pp. 382-393.
Olson et al. "Activatable cell penetrating peptides linked to nanoparticles as dual probes for in vivo fluorescence and MR imaging of proteases," Proc. Nat. Acad. Sci. 107 (2010) 4311-4316.
Hoare et al. "A Magnetically-Triggered Composite Membrane for On-Demand Drug Delivery," Nano Lett. 9 (2009) 3651-3657.
Mornet et al., Magnetic nanoparticle design for medical diagnosis and therapy, J. Mater. Chem., 14 (2004) 2161-2175.

Sexton et al. "A Protective Vaccine Delivery System for In Vivo T Cell Stimulation Using Nanoengineered Polymer Hydrogel Capsules," ACS Nano, vol. 3, No. 11 (2009), pp. 3391-3400.
Alavarez-Lorenzo et al., "Temperature-sensitive chitosan-poly(N-isopropylacrylamide) interpenetrated networks with enhanced loading capacity and controlled release properties" J. Controlled Release 102(3), (2005) 629-641.
Balasubramaniam et al., "Poly(N-isopropylacrylamide)-Coated Superaramagnetic Iron Oxide Nanoparticles Relaxometric and Fluorescence Behavior Correlate to Temperature-Dependent Aggregation" Chem. Mater., 2011, 23, 3348-3356.
Benyettou et al., "Magnetoliposome for alendronate delivery" J. Mater. Chem., 21 (2011) 4813-4820.
Budgin et al. "Functionalization of Magnetic Nanoparticles with Amphiphilic Block Copolymers: Self-Assembled Thermoresponsive Submicrometer Particles" Langmuir 28 (2012) 4142-4151.
Farokhzad et al., "Impact of Nanotechnology on Drug Delivery" ACS Nano 3(1) 2009, 16-20.
Filipa et al., "Polyelectrolyte-Coated Unilamellar Nanometer-Sized Magnetic Liposomes" Langmuir 2009, 25(12), 6793-6799.
Pothayee et al., "Magnetic Block Ionomer Complexes for Potential Dual Imaging and Therapeutic Agents" Chem. Mater. 2012, 24, 2056-2063.
Tai et al. "Thermosensitive liposomes entrapping iron oxide nanoparticles for controllable drug release" Nanotechnology 20 (2009) 135101 (9 pages).
Xu et al. "Controlled Release and Assembly of Drug Nanoparticles via pH-Responsive Polymeric Micelles: A Theoretical Study" J. Phys. Chem. B, 2012, 116 (20), 6003-6009.
Booth et al. Exosomes and HIV Gag bud from endosome-like domains of the T cell plasma membrane. The Journal of Cell Biology, vol. 172, No. 6, Mar. 13, 2006, 923-935.
Heath et al., Varying Polymer Architecture to Deliver Drugs AAPS J. 9 (2007) Nanotechnology and Drug Delivery, article 26 (http://www.aapsi.org) E235-E240.
Jamagin et al. Treatment of cholangiocarcinoma with oncolytic herpes simplex virus combined with external beam radiation therapy. Cancer Gene Therapy 13 (2006) 326-334.
Ding et al., Farnesyltransferase inhibitor tipifamib inhibits Rheb prenylation and stabilizes Bax in acute myelogenous leukemia cells. Haematologica 99 (2014) 60-69.
Kleiner et al. Farnesyl and geranylgeranyl transferase inhibitors: an anti-inflammatory effect. Comment to "Inhibition of protein geranylgeranylation and farnesylation protects against graft-versus-host disease via effects on CD4 effector T cells" haematological 98 (2013) e44-e45.
Karp et al. Multi-institutional phase 2 clinical and pharmacogenomic trial of tipifarnib plus etoposide for elderly adults with newly diagnosed acute myelogenous leukemia. Blood 119 (2012) 55-63.
Hong et al. Phase I Trial of a Combination of the Multikinase Inhibitor Sorafenib and the Farnesyltransferase Inhibitor Tipifarnib in Advanced Malignancies. Clin Cancer Res 15 (2009), 7061-7068.
Kurzrock et al. Phase I Study of Alternate-Week Administration of Tipifarnib in Patients with Myelodysplastic Syndrome. Clin Cancer Res 14 (2008) 509-514.
Haferlach. Molecular Genetic Pathways as Therapeutic Targets in Acute Myeloid Leukemia. (2008) 400-411.
Armand et al. The Emerging Role of Targeted Therapy for Hematologic Malignancies: Update on Bortezomib and Tipifarnib. The Oncologist 12 (2007) 281-290.
Yanamandra et al. Tipifarnib and Bortezomib Are Synergistic and Overcome Cell Adhesion-Mediated Drug Resistance in Multiple Myeloma and Acute Myeloid Leukemia. Clin Cancer Res 12 (2006) 591-599.
Beaupre et al. R115777 induces Ras-independent apoptosis of myeloma cells via multiple intrinsic pathways. Mol Cancer Ther 3 (2004) 179-186.
Leite et al. PE and PS Lipids Synergistically Enhance Membrane Poration by a Peptide with Anticancer Properties. Biophysical Journal 109 (2015) 936-947.
Bakalova et al., "Quantum Dot-Conjugated Hybridization Probes for Preliminary Screening of siRNA Sequences" J. Am. Chem. Soc., (2005), 127 (32), pp. 11328-11335.

(56) References Cited

OTHER PUBLICATIONS

Derfus et al. "Targeted Quantum Dot Conjugates for siRNA Delivery" Bioconjugate Chem., vol. 18, No. 5 (2007) pp. 1391-1396.

Ebenstein et al. "Combining atomic force and fluorescence microscopy for analysis of quantum-dot labeled protein-DNA complexes" J. Molecular Recognition, vol. 22, issue 5 (2009), pp. 397-402.

Gill et al. "Fluorescence Resonance Energy Transfer in CdSe/ZnS—DNA Conjugates: Probing Hybridization and DNA Cleavage" J. Phys. Chem. B, vol. 109, (2005), pp. 23715-23719.

Joo et al. "Enhanced Real-Time Monitoring of Adeno-Associated Virus Trafficking by Virus-Quantum Dot Conjugates" ACS Nano, vol. 5, No. 5 (2011), pp. 3523-3535.

Lim et al. "Specific Nucleic Acid Detection Using Photophysical Properties of Quantum Dot Probes" Anal. Chem., vol. 82, No. 3 (2010), 886-891.

Taylor et al., "Glycogen Synthase Kinase 3 Inactivation Drives T-bet-Mediated Downregulation of Co-receptor PD-1 to Enhance CD8+ Cytolytic T Cell Responses," Immunity, Feb. 16, 2016, vol. 44, No. 2, pp. 274-286.

Husseini el al., "Ultrasonic-Activated Micellar Drug Delivery for Cancer Treatment," J Pharm Sci, May 27, 2008, vol. 98, No. 3, pp. 795-811.

Kong et al., "Efficacy of Liposomes and Hyperthermia in a Human Tumor Xenograft Model: Importance of Triggered Drug Release," Cancer Research, Dec. 15, 2000, vol. 60, pp. 6950-6957.

Phenix et al., "High Intensity Focused Ultrasound Technology, Its Scope and Applications in Therapy and Drug Delivery," Journal of Pharmacy & Pharmaceutical Sciences, Mar. 31, 2014, vol. 17, No. 1, pp. 136-153.

PCT Form 210, International Search Report for PCT/US2018/054880, dated Jan. 9, 2019.

PCT Form 237, Written Opinion of the International Searching Authority for PCT/US2018/054880, dated Jan. 9, 2019.

Narayanan et al., Mimicking cellular transport mechanism in stem cells through endosomal escape of new peptide-coated quantum dots. Scientific Reports 3, Jul. 15, 2013, article No. 2184, 6 pages.

Gao et al., Autologous tumor lysate-pulsed dendritic cell immunotherapy with cytokine-induced killer cells improves survival in gastric and colorectal cancer patients. PLoS One, vol. 9, issue 4 (2014), pp. 1-9.

Helfand et al. "A Genetic-Based Approach to Personalized Prostate Cancer Screening and Treatment." Curr Opin Urol., Jan. 2015, 25(1): pp. 1-11.

M.A. Lewis, R.M. Staruch, R. Chopra, Thermometry and ablation monitoring with ultrasound, Int. J. Hyperth. 31 (2015), pp. 163-181.

R.M. Arthur, W.L. Straube, J.W. Trobaugh, E.G. Moros, Non-invasive estimation of hyperthermia temperatures with ultrasound, Int. J. Hyperth. 21 (2005), pp. 589-600.

R.M. Arthur, W.L. Straube, J. Trobaugh, E.G. Moros, In vivo change in ultrasonic backscattered energy with temperature in motion-compensated images, Int. J. Hyperth. 24 (2008), pp. 389-398.

R.M. Arthur, D. Basu, Y. Guo, J.W. Trobaugh, E.G. Moros, 3-D in vitro estimation of temperature using the change in backscattered ultrasonic energy, IEEE Trans. Ultrason. Ferroelectr. Freq. Control. 57 (2010), pp. 1724 1733.

C. Simon, P. VanBaren, E. Ebbini, Two-dimensional temperature estimation using diagnostic ultrasound, IEEE Trans. Ultrason. Ferroelectr. Freq. Control. 45 (1998), pp. 1088-1099.

D. Liu, E.S. Ebbini, Real-time 2-D temperature imaging using ultrasound, IEEE Trans. Biomed. Eng. 57 (2010), pp. 12-16.

E.S. Ebbini, C. Simon, D. Liu, Real-time ultrasound thermography and thermometry [Life Sciences], IEEE Signal Process. Mag. 35 (2018), pp. 166-174.

K.W.A. Van Dongen, M.D. Verweij, A feasibility study for non-invasive thermometry using non-linear ultrasound, Int. J. Hyperth. 27 (2011), pp. 612-624.

B. Maraghechi, M.H. Hasani, M.C. Kolios, J. Tavakkoli, Temperature dependence of acoustic harmonics generated by nonlinear ultrasound wave propagation in water at various frequencies, J. Acoust. Soc. Am. 139 (2016), pp. 2475-2481.

B. Maraghechi, M.C. Kolios, J. Tavakkoli, Temperature dependence of acoustic harmonics generated by nonlinear ultrasound beam propagation in ex vivo tissue and tissue-mimicking phantoms, Int. J. Hyperth. 31 (2015), pp. 666-673.

M. Bayat, J.R. Ballard, E.S. Ebbini, In vivo ultrasound thermography in presence of temperature heterogeneity and natural motions, IEEE Trans. Biomed. Eng. 62 (2015), pp. 450-457.

B. Maraghechi, Feasibility of noninvasive thermometry in hyperthermia regime using harmonics generated by nonlineai ultrasound wave propagation, Ryerson University, 2016, pp. 1-130.

F. Butt, High performance computing for linear acoustic wave simulation, Ryerson University, 2011, pp. 1-127.

F. Butt, A. Abhari, J. Tavakkoli, An application of high performance computing to improve linear acoustic simulation, in: Spring Simul. Multi-Conference, Boston, Massachusetts, 2011: pp. 71-78.

E. Shaswary, Y. Xu, J. Tavakkoli, Performance study of a new time-delay estimation algorithm in ultrasonic echo signals and ultrasound elastography, Ultrasonics. 69 (2016), pp. 11-18.

B.C. Giovanella, A.C. Morgan, U.S. Stehlin, L.J. Williams, Selective Lethal Effect of Supranormal Temperatures on Mouse Sarcoma Cells, Cancer Res. 33 (1973), pp. 2568-2578.

\* cited by examiner

CANCER TREATMENT METHODS USING THERMOTHERAPY AND/OR ENHANCED IMMUNOTHERAPY

This patent application is a continuation-in-part of U.S. patent application Ser. No. 14/976,321, entitled "Method to Visualize Very Early Stage Neoplasm or Other Lesions", filed Dec. 21, 2015, the disclosure of which is hereby incorporated by reference as if set forth in its entirety herein.

This patent application also is a continuation-in-part of International Patent Application Ser. No. PCT/US2018/054880, entitled "Cancer Treatment Methods Using Thermotherapy and/or Enhanced Immunotherapy", filed Oct. 8, 2018, which claims priority to U.S. Provisional Patent Application No. 62/569,592, entitled "Cancer Treatment Methods Using Thermotherapy and/or Enhanced Immunotherapy", filed on Oct. 8, 2017, U.S. Provisional Application No. 62/577,485, entitled "Cancer Treatment Methods Using Thermotherapy and/or Enhanced Immunotherapy", filed on Oct. 26, 2017, U.S. Provisional Application No. 62/614,456, entitled "Cancer Treatment Methods Using Thermotherapy and/or Enhanced Immunotherapy", filed on Jan. 7, 2018, and U.S. Provisional Patent Application No. 62/720,258, entitled "Cancer Treatment Methods Using Thermotherapy and/or Enhanced Immunotherapy", filed on Aug. 21, 2018; the disclosure of each of which is hereby incorporated by reference as if set forth in their entirety herein.

In one or more embodiments, a method is disclosed for evaluating treatment outcome in a patient having a genetic predisposition for a malignant neoplasm before clinical manifestation of the neoplasm can be seen radiographically. The method permits visualization of any tumor, whether located externally on a patient's body or located internally in the body, and as small as 2 mm in diameter, producing a biomarker, either a biomarker specific for the tumor or a general biomarker.

In general, a biomarker indicates a disease process. As subsequently described, a biomarker can be a protein, antigen, enzyme, hormone, carbohydrate, toxin, DNA, an organism such as bacteria, tumor cell, exosome, or indirectly an antibody, present in a liquid biopsy specimen. It can be produced by the plasma cells, against a tumor antigen, etc.

The method uses antibodies conjugated with nanoparticles which include but are not limited to quantum dots, with the conjugated form collectively termed functionalized nanoparticles, that are heated under specified conditions to produce a photoacoustic signal (for use on the body surface or for use in reachable cavities) that is then visualized to locate the tumor to which the nanoparticles are attached. Nanoparticles may be used for qualitative and quantitative assessment of an analyte in the blood or other tissue using photoacoustic technology, U.S. Pat. No. 8,554,296. As previously stated, as used herein, unless specifically stated otherwise, nanoparticles include but are not limited to quantum dots.

Early stage small neoplastic cells produce biomarkers that are either specific to the tumor cells or that represent the body's response to the tumor as an antibody. The biomarkers can be proteomic, genetic, epigenetic or glycomic biomolecules. These biomolecules can be recognized in the patient's tissue samples or in the blood. Their existence can be demonstrated thus far chemically using, e.g., immunoassay or PCR methods. Quantitation of these biomarkers is also important to determine disease progression and prognosis.

Biomarkers for many diseases are found in the blood. As subsequently disclosed, biomarkers detected in a liquid biopsy sample are used to generate antibodies against them using known methods in the art. The anti-tumor antibodies are used to coat nanoparticles in the inventive method, where a lesion can be imaged regardless of the lesion size or location in the body. The method is not limited to tumor detection and/or therapy. As only one example, detecting an antibody against anti-β-amyloid protein plaque present in Alzheimer's disease in a liquid biopsy specimen, the method renders the plaque visible with the nanoparticles and accessible to the inventive treatment. As another example, the method can also be used to detect and/or treat inflammatory processes, etc.

The inventive method is applicable to any processes or diseases that produce a biomarker detectable in a liquid biopsy specimen. It is applicable to a lesion including an abscess, an ulcer, a tumor either benign or malignant, an ischemic area of stroke and/or an area of the brain affected by a stroke whether visible or microscopically.

In one embodiment, many biomarkers may be combined to coat nanoparticles. Over a thousand proteins are differentially expressed in human cancers and thus may serve as biomarkers. Such proteins play a role in cancer-related processes such as angiogenesis, apoptosis, cell differentiation, cell signaling, hematopoiesis, hormonal control, immune reactions, etc. Exemplary biomarkers include in the claim, but are not limited to, carcinoembryonic antigen (CEA) for both malignant pleural effusion and peritoneal cancer dissemination; human epidermal growth factor receptor 2 (HER-2/neu) for stage IV breast cancer; bladder tumor antigen for urothelial cell carcinoma; thyroglobulin for thyroid cancer metastasis; α-fetoprotein for hepatocellular carcinoma; prostate specific antigen (PSA) for prostate cancer; cancer antigen 125 (CA 125) for non-small cell lung cancer; cancer antigen 19.9 (CA 19.9) for pancreatic cancer; cancer antigen 15.3 (CA 15.3) for breast cancer; the combination of leptin, prolactin, osteopontin, and insulin-like growth factor II (IGF-II) for ovarian cancer; the combination of CD98, fascin, secreted chain of the polymeric immunoglobulin receptor (sPIgR), and 14-3-3 eta proteins for lung cancer; troponin I for myocardial infarction, and B-type natriuretic peptide for congestive heart failure. While the previous nine proteins are the only approved markers for cancer testing to date, they are but a small fraction of the total number of available biomarkers, and their sensitivity and specific vary.

Other common biomarkers include the estrogen receptor/progesterone receptor (ER/PR), HER-2/neu, and epidermal growth factor receptor (EGFR) for breast cancer, and tissue inhibitor of metalloproteinases (TIMP-1)-associated with serum HER2-positive breast cancer; Kirsten Ras oncogene (KRAS) and UDP glucuronosyltransferase family 1 member A (UGT1A1) for colorectal cancer; HER-2/neu for gastric cancer, c-KIT, CD20 antigen, CD30, and factorilnteracting with PAPOLA and CPSF1-platelet-derived growth factor receptor alpha fusion protein (FIP1L1-PDGRF alpha), and platelet-derived growth factor receptor (PDGFR) for gastrointestinal stromal tumor (GIST); Philadelphia Chromosome (BCR/ABL)/PML/RAR alpha and anaplastic lymphoma kinase (TPMT/UGT1A1/ALK EGFR) for leukemia/lymphoma; KRAS/EGFR for lung cancer, and BRAF and S100 for melanoma.

Other examples of biomarkers include tumor suppressors that are lost in cancers, such as Breast Cancer Gene 1 (BRCA1), Breast Cancer Gene 2 (BRCA2); RNA such as mRNA, microRNA; proteins found in body fluids or tissue such as prostate specific antigen and CA-125; gene and protein based biomarkers; and nonspecific biomarkers such as glycosaminoglycans in body fluids; alkaline phosphatase and urinary hydroxyproline in skeletal involvement; hyaluronic acid excretion and urinary hydroxyproline in bone disease, and combinations thereof.

In malignancies, the biomarkers may be released into the circulation either prior to or after the tumor has grown sufficiently to become metastatic. Small tumors (less than about 2 mm) seldom have any clinical manifestations, however even such small tumors can release chemical and/or biomarkers into the circulation.

The existence of biomarkers in the circulation has been known, but has not met the threshold for locating tumor cells that could not be imaged radiographically or by ultrasound as long as the tumors were asymptomatic. Available imaging methods such as x-ray, magnetic resonance imaging (MRI), functional MRI, computed tomography (CT) scans, CT ultrasound, etc. may not permit visualization of lesions smaller than about 3 mm in diameter. This has been the case for most malignant tumors, or when a malignant tumor is created from a benign precursor lesion such as nevus, breast unspecific cyst or unspecific scar, prostate tumors along with benign prostate hypertrophy or uterus cancer inside the uterus fibroma, melanoma inside a skin nevus or in a seborrheic keratosis, etc. Moreover, it is often difficult to follow a cancerous tumor which has been irradiated but may still harbor malignant cells, and that can start growing with time and metastasize before it shows a local growth that is detected by conventional imaging or other methods.

The diagnosis of a malignant tumor may be extremely difficult, even when a tumor is visible clinically or radiologically, e.g. a uterus fibroma that may have some malignant transformation. Moreover, a diagnosis also affects the decision whether or not and also how to remove the tumor. As one example, accessing the uterus through a small incision, and removing the tumor piece by piece using an endoscope and a cutting probe, has a fast post-operative recovery. Such a method is in contrast to completely removing the uterus with the tumor intact out of caution that the tumor may harbor neoplastic cells, but using a large incision with significantly higher operative risks and post-operative complication probabilities. Another, more problematic example, is the decision for a woman having genetic disposition to breast cancer without any physical or radiological manifestation. The woman must endure the stress and fear not knowing if or when she may develop breast cancer, and must consider prophylactic removal of both breasts. As another example, a personal decision whether or not to undergo radiation therapy when a nevus is discovered under the retina, and biopsy results that often do not provide definitive information because of the diversity of the cells in the entire area of the tumor.

When the tumor site is unknown, locating a biomarker in the circulation may be akin to finding a needle in a hay stack. For any particular tumor or cancer, not all biomarkers are even known. Similarly, finding a micro DNA in the circulation may not provide an answer when the tumor is either invisible or has already metastasized. An example of this occurs in patients with uveal melanomas, having a mortality rate of about 50%, even if the tumors undergo radiation, at the time the ophthalmologist discovers the tumor. This points to the fact that a malignant tumor can metastasize very early, at times even when the size of the tumor is about 2 mm in diameter which is equal to about one million cells. In general, these lesions do not have any symptoms.

The inventive method makes it possible to evaluate a patient with genetic predisposition of a malignant neoplasm before its clinical manifestation can be seen radiographically.

Figure 1:
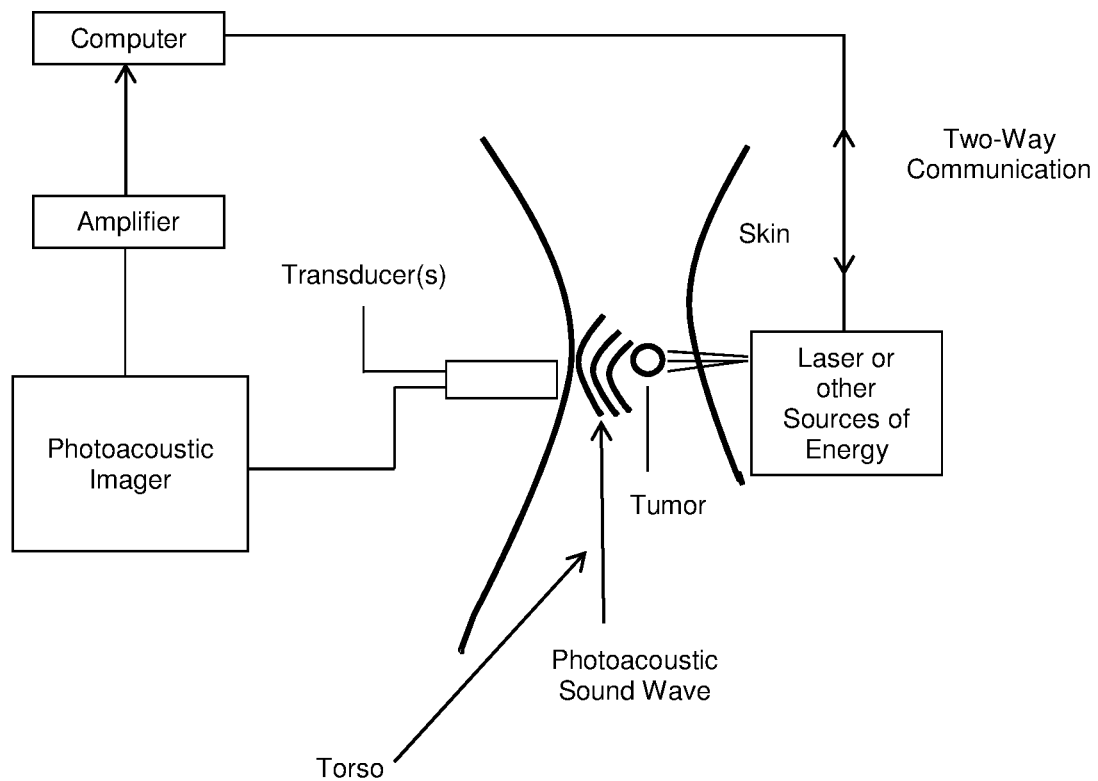
FIG. 1 illustrates a schematic diagram of a cancer treatment and imaging system, according to an embodiment of the invention.

In one embodiment, the presence of one or more biomarkers is evaluated in any body fluid or organ. Exemplary bodily fluids include, but are not limited to, urine, blood, cerebrospinal fluid (CSF), eye cavity fluid, tear film, sputum, fluid obtained from the trachea, bronchi, abdominal cavity, vagina, uterus etc. The biomarkers are analyzed in vitro by methods known in the art, e.g., immunoassays including enzyme-linked immunoassay (ELISA), Western blots, fluorescence in situ hybridization (FISH), polymerase chain reaction (PCR), etc. The biomarkers are then conjugated with functionalized antibody coated nanoparticles and/or quantum dots, as known in the art.

In one embodiment, one obtains a liquid biopsy sample. Such a sample may be obtained from, e.g., blood, urine, cerebrospinal fluid (CFS), aqueous or vitreous or abdominal cavity fluid, lymph node fluid, bladder fluid, milk duct fluid, sputum, gastric fluid, bile duct fluid, sinus fluid, etc. The patient may or may not have any clinical symptom. The patient may or may not have history of a family disposition for tumors in and/or cancer of the breast, brain, lung, prostate, ovary, pancreas, etc., or a genetic abnormality leading to progression in diseases such as, e.g., Alzheimer's, Parkinson's, post traumatic brain syndrome, brain tumor, other neurological disease, age related macular degeneration, an infectious disease, an immune response, etc. The method evaluates the components of the sample for cell free nucleic acid-based biomarkers including but not limited to micoRNA and microDNA; protein-based biomarkers, extracellular vesicle (EV)-based biomarkers that are contained within exosomes, extracellular vesicles, or microvesicles, and circulating tumor cell (CTC)-based biomarkers. The method uses methodologies such as next generation sequencing (NGS) or recombinant affinity reagents fabricated into nanostructures such as carbon nanotubes, nanowires, quantum dots, or gold nanoshells, to enhance their detection with the use of, e.g., surface-enhanced Raman scattering (SERS), as known in the art.

For example, if a known tumor exists and there is a known biomarker for the tumor, one may have or prepare an antibody against the tumor to be used in both imaging and therapy. Large tumors with symptoms can be imaged, but before the inventive method, there was a problem when a biomarker was present in a liquid biopsy specimen but the tumor was invisible, e.g., an early stage of a tumor, and there was no symptomatic or radiographic evidence of the tumor.

Detecting a tumor biomarker, typically a protein or a glycoprotein, in a liquid biopsy specimen is facilitated by the inventive methods. Once detected, an antibody against that tumor biomarker can be prepared. The antitumor biomarker antibody is used to locate the tumor. Antibody production is a well-known method in the art, and it will be appreciated that the antibody against either or both of the tumor biomarker and the tumor cell may be recombinant, monoclonal, polyclonal, or an aptamer. The prepared antitumor cell antibodies are conjugated with nanoparticles and administered to a patient, where they target the tumor cells and can be detected and/or treated. Detection is by photoacoustic imaging or by some other type of imaging technology. Treatment is at least by one of thermal energy. The photoacoustic detection and thermal treatment is described herein.

In one embodiment, any specific tumor related biomarker may be used. One example uses trastuzumab or herceptin, a recombinant monoclonal antibody, against the oncogene HER-2, previously mentioned, which is a member of the human epidermal growth factor receptor (HER/EGFR/ERBB) family. Other examples of known monoclonal antibodies or biologics include, but are not limited to, rituximab, cetuximab, racotunomab, obinotuzumab, pertuzumab, belaniatumomab, bevacizumab, nivolumab, ofatumumab, botezomib, daratumumab, ipilumumab, pembrolizumab, and daratumumab.

In one embodiment, in the absence of a specific biomarker, antibodies against biomarkers that are shared by a number of the tumors may be used. Such biomarkers include glycosaminoglycan, which is specific for a group of cancers such as bladder, gastrointestinal, glioblastoma, etc. Antibodies against such biomarkers are then conjugated with nanoparticles, termed functionalized nanoparticles. The term "functionalized" indicates nanoparticles that have been coated to render them soluble, biocompatible, and/or targeted by conjugating them with a biomolecule such as an antibody.

In one embodiment, the nanoparticle may be one or more of the following compounds or contain one or more of the following components: quantum dots, nanowires, nanotubes, nanoshells, nanocages, perovskites, nanoparticles that are magnetic such as iron or iron oxide, paramagnetic, or nanoparticles that are non-magnetic such as gold, gold-silica, gold-iron, silica coated gold nanospheres and nanorods, ferritic, quartz, graphene, carbon, zinc oxide, piezoelectric, etc. Any of these nanoparticles, alone or in combination, may be conjugated or otherwise associated with the biomarkers' antibodies, using methods known in the art.

In another embodiment, self-assembling bio/nano hybrid material consisting of two constituents at the nanometer or molecular level composed of inorganic and organic compounds, having amphiphilic characteristics, i.e., hydrophilic and lipophilic components or micelles, which may be radioactive (e.g., $Cu^{64}$) or radioactive (e.g., tin) are prepared with biocompatible coatings and administered in the body for both therapy and imaging.

In one embodiment, the functionalized nanoparticles travel in the body and attach to receptors of desired cells, e.g., tumors, Alzheimer's plaque, drusen of the retina, etc. These nanoparticles are imaged by applying external thermal energy and/or by applying a reversible or alternating magnetic field. The thermal energy causes the nanoparticles to expand, producing an ultrasound wave in the tissue. The ultrasound wave can be detected by an ultrasonic receiver which is imaged in two to three dimensional formats as a tomogram. In another embodiment, the plaques in Alzheimer's disease, and the drusen in age related macular degeneration, are rendered visible using silica coated nanoparticles <2 nm in diameter administered with turmeric, glycosaminoglycan, amyloid antibody, or percolan, etc. and are quantified. In another embodiment, the nanoparticles are conjugated with antibodies, medications, sterols, antibiotics, antifungals, antibacterials, antiproliferative agents, etc. that can be released from silica coated gold nanoparticles when coated with thermosensitive polymers, e.g., chitosan coated nanoparticles heated to 40° C.-42° C., to treat various diseases including bacteria, fungi, parasites, plaque, drusen, etc. In another embodiment, the plaques and drusen can be quantified by imaging using light, MRI, photoacoustic technology imaging, etc.

In another embodiment, the functionalized anti-biomarker-conjugated nanoparticle, ranges in size from 1 nm to 900 nm. In another embodiment, the functionalized biomarker ranges in size from 1 nm to 8 nm, chosen to enhance their elimination through the kidney for facilitated clearance.

In one embodiment, the nanoparticles are rendered magnetic by coating with a thin film of iron oxide prior to their conjugation with biomarkers' antibodies.

In one embodiment, the nanoparticles are rendered more biocompatible by coating with a compound, including but not limited to the following: (poly)ethylene glycol, cell penetrating peptide (CPP), activating CPP (ACPP), biotin, streptavidin, etc., as known in the art, prior to their injection in the body.

Thermal energy in the form of electromagnetic radiation, ultrasound, or an alternating magnetic field is applied, under the control of a photoacoustic imaging system, to the organ suspected of potentially harboring an as yet invisible neoplasm. The thermal energy applied increases the temperature of the exposed nanoparticle, and creates a photoacoustic or thermoacoustic image or tomogram of the accumulated heated nanoparticles. This image or tomogram represents a suspected neoplasm in that organ, and is compared to an image taken without the thermal application radiographically.

In one embodiment, one administers functionalized antibody-coated nanoparticles that, once attached to tumor cells, become visible with a photoacoustic imaging unit that corroborates with an image obtained or not seen with other technology such as ultrasound, MRI, PET, CT scan, etc. In one embodiment, the images obtained with other instruments are either overlapped using a processor or are taken simultaneously during photoacoustic or thermoacoustic imaging. In one embodiment, after administration of the antibody-coated nanoparticle, an MRI image is overlapped with the photoacoustic image and compared by a processor to verify the changes in the imaged area.

In one embodiment, the nanoparticles are incorporated in liposomes. In this embodiment, they may contain medications that, upon attainment of a specific tumor temperature, are released. The type of medication is not limited, and can include anti-bacterial, anti-viral, anti-fungal, antineoplastic, anti-inflammatory such as acetyl cycline, anti-beta-amyloid protein, other antibodies, non-steroidal anti-inflammatory drugs, immune stimulating agents, anti-VEGF agents, anti-aggregation agents such as sterols, etc.

In another embodiment, antibody-coated nanoparticles conjugated with thermosensitive polymers, such as chitosan, carrying any medication including but not limited to sterol, squalamine, lanosterol, is administered to a patient having a neurologic pathology such as Alzheimer's disease, Parkinson's disease, or age related retinal drusen, etc. In this embodiment, administration is either intravenous or local in the cerebrospinal fluid or vitreous cavity, respectively, or at another local site. After controllably increasing the temperature of the functionalized nanoparticle to between 40° C.-43° C. by increased energy delivery through a thermal delivery source, under the control of the photoacoustic (or thermoacoustic) imaging system and a processor, the temperature-sensitive coating polymers, such as chitosan, melts and release medications specific to the pathology. For example, a medication to dissolve amyloid plaques would be administered to a patient with Alzheimer's disease; a medication to remove retinal drusen would be administered to a patient with age-related retinal disease, etc.

In one embodiment, the functionalized nanoparticle, e.g., a nanoshell, nanocage, etc., is combined with biodendrimers that are conjugated with biomarkers and monoclonal antibodies and/or genes, e.g., siRNA, mRNA, etc., for simultaneous visualization and therapy.

In one embodiment, the functionalized nanoparticle, e.g., a nanoshell, nanocage, etc., is combined with biodendrimers that are conjugated with biomarkers and monoclonal antibodies and/or genes, e.g., siRNA, mRNA, and CRISPR Cas9 and Krüppel associated box (KRAB) domain to silence the tumor gene etc., for simultaneous visualization and therapy.

In another embodiment, after thermal imaging one increases the temperature of the functionalized nanoparticles. This is achieved by increased energy delivered by a thermal delivery source under the control of the photoacoustic or thermoacoustic imaging system connected to a processor. The energy delivery unit increases the temperature of the functionalized nanoparticles to 42° C.-43° C. to melt the temperature-sensitive coating polymers, such as chitosan, and release anticancer medications, or inhibitory genes, siRNA, miRNA, and CRISPR Cas9 and KRAB domain to neutralize a tumor gene or checkpoint inhibitors, or introduce missing genes, or add any other genes for gene editing from the thermosensitive coating of the nanoparticles along with a CRISPR complex to modify the genetic composition of the tumor cells, etc. In another embodiment, the temperature of the functionalized nanoparticles is increased, by the thermal delivery unit via a processor under the control of the photoacoustic or thermoacoustic imaging unit, to image the temperature and control it to 45° C.-47° C., to 47° C., or to 50° C. to kill the suspected tumor to which the antibody-coated nanoparticles are attached.

In one embodiment, one synthesizes hybrid, very small (1 nm-8 nm) gold silica nanoparticles that have a dual function, the nanoparticles antibody coated for imaging, and having photovoltaic and magnetic properties, to release one or more gene(s) or medication(s) at certain temperatures, creating a photoacoustic response for imaging in the body by light stimulation in the eye for simultaneous imaging and therapy.

In one embodiment, using antibody coated quantum dots and light of a specific wavelength that is absorbed by the quantum dot and emits light of a different wavelength, one can render the moving tumor cells and extracellular vesicle visible attached to the quantum dots in the retinal or choroidal vessels, or vessels and tumors of the skin, or tumors located beneath the skin and their feeding vessels, by light absorbed by the quantum dots circulating in the vessels, as is done in fluorescence angiography with appropriate filters and camera.

In another embodiment, a gold quantum dot in a mesoporous silica shell or cage is coated with an antibody or a biomarker to any cell, e.g., neuronal or tumor cells, retinal drusen, Alzheimer plaques, etc. for delivering medication or gene to an organ, e.g., to the retina or brain.

In another embodiment, the extent of plaque or drusen, as an indicator of disease progression in the brain or eye, respectively, can be evaluated by conjugating nanoparticles with antibodies to glycosaminoglycan, heparin sulfate, glycosaminoglycan, and/or heparin sulfate proteoglycan, and injecting the composition into the body or locally to adhere to plaques or drusen for diagnosis, quantitation, and/or therapy with antibodies and medication.

In another embodiment, the nanoparticles are used for simultaneous imaging and thermotherapy of very small tumors. The nanoparticles are heated to a temperature ranging from 41° C.-43° C., releasing anti-cancer medication, along with inhibitory siRNA, or modify a gene using the CRISPR cas9 system or another CRISPR system, additionally releasing checkpoint inhibitors such as CTLA-4 or PD-1 along with tumoricidal vectors, etc.

In one embodiment, the nanoparticles are rendered radioactive by coating with the nanoparticles with alpha or beta radiators that are antibody specific or nonspecific biomarkers of the tumor. The nanoparticles can also be coated with heat sensitive polymers, including but not limited to chitosan, PEG, poly amino esters, etc.

In one embodiment, checkpoint inhibitors defined as immune system components that act as co-stimulatory or co-inhibitory molecules, poisons such as bee or snake venom, or other toxic agents that damage tumor cell membranes, or interleukin-2 (IL-2), or toll-like receptor 7 (TLR7), or genes that inhibit tumor growth, siRNA, siDNA, miRNA, mDNA along with the CRISPR-cas9 complex with and without KRAB domain or variations of these may be used to silence the tumor gene.

In one embodiment, the nanoparticles are coated with a specific or a nonspecific biomarker such as glycosaminoglycan and injected into the circulation, into a body fluid such as the lymphatic system or cerebrospinal fluid (CSF), or inside a body cavity. Examples of injection sites include, but are not limited to, eye, sinuses, abdominal cavity, bladder, uterus, etc. The nanoparticles may also be injected into the breast ducts, e.g., through the nipple, inside the brain, into the prostate or other organ, or may even be applied topically. The injected nanoparticles circulate and seek cells bearing a receptor to their antibody, or cells with specific receptors or biomolecules, and readily attach within minutes or hours.

In one embodiment, specific or non-specific biomarkers' antibodies are conjugated with nanoparticles and injected either into circulation or locally into a body cavity. The nanoparticles travel and seek cells bearing specific receptors or biomolecules, and attach within a few hours. The patient's body or organ is then scanned, with the thermal energy producing radiation or an alternating or reversible magnetic field to heat the nanoparticles. Using photoacoustic or thermoacoustic technology, the sound wave generated by the thermal expansion of the nanoparticle induced by absorption of the thermal energy is recorded. The sound wave signals may originate from any part of the body, or from a specific organ.

In one embodiment, an alternating magnetic field produces heat in magnetic nanoparticles as a result of rapid circular or semicircular motion of the nanoparticles. The patient's body is scanned within the reversible magnetic field, and the photoacoustic or thermoacoustic sound is recorded as a temperature profile of the site of the nanoparticle/cell membrane imaged and location of the lesion is verified.

In another embodiment, other sources of thermal energy are used. Such sources include, but are not limited to, electromagnetic radiation, visible light, invisible light, infrared radiation, microwaves, or radiofrequency waves, etc. The nanoparticles are heated from body temperature of 37° C. to 40° C. or 43° C., or if needed to 45° C. At the desired temperature, e.g., 41° C.-43° C., the heat sensitive coating of the nanoparticle melts, releasing its cargo of, e.g., medication, gene, etc., thus facilitating or enhancing passage of these compounds through the membrane of the neoplastic cells.

In another embodiment, use of a photoacoustic or thermoacoustic technology unit controls the thermal delivery unit and the thermal energy delivered to the nanoparticles to maintain or reach a predetermined temperature for a desired time.

In one embodiment, the temperature rise of the nanoparticles expands them, producing a photoacoustic or thermoacoustic sound wave. This photoacoustic or thermoacoustic sound wave is recorded by one or multiple ultrasonic receivers located on the patient's skin. The signal can be obtained from any part of the body, or from a specific organ, since the signal travels through the body as a wave. The signal or sound pulse is converted to an electric pulse in the receiver, then is amplified and imaged on a monitor. A processor produces a two- or three-dimension image of the lesion, localizing the location of the sound and indicating the size of a lesion and its temperature by the amplitude of the sound pulse.

In one embodiment, photoacoustic or thermoacoustic imaging is used for a very early stage diagnosis of cancerous lesion that are less than 2 mm in diameter, which are radiographically invisible without knowing their exact location in the body (e.g., for the tissue surface in the eye and visible cavities).

In one embodiment using photoacoustic technology and a specific or non-specific tumor biomarker, a very small lesion (<2 mm in diameter) is imaged in the body when the tumor has not caused any clinical symptom. The inventive method thus is used to differentiate a malignant lesion from a benign lesion, even if the cancerous lesion is inside a begin lesion. It is noteworthy that biopsy of these very small tumors, even when the lesion is visible, e.g., on skin or under the retina, may not yield malignant cells if the biopsy is performed on a part of the lesion that contains benign cells. With tumors in the brain, it is most often the case that the tumors will not be noted, absent a neurological symptom.

In one embodiment, the inventive method is used with specific biomarkers of a tumor such as breast cancer, prostate cancer, glioma, pancreatic malignancies, along with nonspecific biomarkers. The location and size of a malignant tumor in any organ is imaged in a patient with a genetic propensity to develop a tumor. The thermal energy may also be applied, if desired, to treat the lesion simultaneously with providing the photoacoustic or thermoacoustic effect. Subsequent evaluation of the level of these biomarkers in the blood indicate if the lesion was damaged or eliminated by the method, including use of medicaments and/or other treatment agents delivered by the method as cargo in the nanoparticles.

In one embodiment, a combination of biomarkers can be used in an early stage. For example, specific or nonspecific bio-markers such as glycosaminoglycans can be used in imaging a malignant lesion using antibody-coated nanoparticles to photoacoustically or thermoacoustically image the presence of a very small early stage tumor anywhere in the body.

In another embodiment, the inventive method is employed to determine residual tumor cells that may have been left at the site of a tumor resection or elsewhere in the body, and to treat or eliminate the residual tumor cells.

In another embodiment, the functionalized nanoparticles are conjugated with one of the recombinant, monoclonal, or polyclonal antibodies or aptamers known in the art and administered along with either one or more toxin(s) or antibodies, along with a medication that is provided at a much lower dose systemically to kill the already compromised tumor cells. Monoclonal antibodies that may be used include, but are not limited to, those shown in Table 1, e.g., rituximab, obinuzumab, oftumumab, etc.

TABLE 1

| Name | Trade name | Type | Source | Target | Use |
|---|---|---|---|---|---|
| 3F8 | | mab | mouse | GD2 | neuroblastoma |
| 8H9 | | mab | mouse | B7-H3 | neuroblastoma, sarcoma, metastatic brain cancers |
| Abagovomab | | mab | mouse | CA-125 (imitation) | ovarian cancer |
| Abciximab | ReoPro | Fab | chimeric | CD41 (integrin alpha-IIb) | platelet aggregation inhibitor |
| Abituzumab | | mab | humanized | CD51 | cancer |
| Abrilumab | | mab | human | integrin α4β7 | inflammatory bowel disease, ulcerative colitis, Crohn's disease |
| Actoxumab | | mab | human | *Clostridium difficile* | *Clostridium difficile* infection |
| Adalimumab | Humira | mab | human | TNF-α | Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| Adecatumumab | | mab | human | EpCAM | prostate and breast cancer |

TABLE 1-continued

| Name | Trade name | Type | Source | Target | Use |
|---|---|---|---|---|---|
| Aducanumab | | mab | human | beta-amyloid | Alzheimer's disease |
| Afelimomab | | F(ab')$_2$ | mouse | TNF-α | sepsis |
| Afutuzumab | | mab | humanized | CD20 | lymphoma |
| Alacizumab pegol | | F(ab')$_2$ | humanized | VEGFR2 | cancer |
| ALD518 | | ? | humanized | IL-6 | rheumatoid arthritis |
| Alemtuzumab | Campath, MabCampath | mab | humanized | CD52 | Multiple sclerosis |
| Alirocumab | | mab | human | NARP-1 | hypercholesterolemia |
| Altumomab pentetate | Hybri-ceaker | mab | mouse | CEA | colorectal cancer (diagnosis) |
| Amatuximab | | mab | chimeric | mesothelin | cancer |
| Anatumomab mafenatox | | Fab | mouse | TAG-72 | non-small cell lung carcinoma |
| Anetumab ravtansine | | mab | human | MSLN | cancer |
| Anifrolumab | | mab | human | interferon α/β receptor | systemic lupus erythematosus |
| Anrukinzumab (=IMA-638) | | mab | humanized | IL-13 | ? |
| Apolizumab | | mab | humanized | HLA-DR ? | hematological cancers |
| Arcitumomab | CEA-Scan | Fab' | mouse | CEA | gastrointestinal cancers (diagnosis) |
| Ascrinvacumab | | mab | human | activin receptor-like kinase 1 | cancer |
| Aselizumab | | mab | humanized | L-selectin (CD62L) | severely injured patients |
| Atezolizumab | | mab | humanized | CD274 | cancer |
| Atinumab | | mab | human | RTN4 | ? |
| Atlizumab (=tocilizumab) | Actemra, RoActemra | mab | humanized | IL-6 receptor | rheumatoid arthritis |
| Atorolimumab | | mab | human | Rhesus factor | hemolytic disease of the newborn[citation needed] |
| Bapineuzumab | | mab | humanized | beta amyloid | Alzheimer's disease |
| Basiliximab | Simulect | mab | chimeric | CD25 (α chain of IL-2 receptor) | prevention of organ transplant rejections |
| Bavituximab | | mab | chimeric | phosphatidylserine | cancer, viral infections |
| Bectumomab | LymphoScan | Fab' | mouse | CD22 | non-Hodgkin's lymphoma (detection) |
| Begelomab | | mab | mouse | DPP4 | ? |
| Belimumab | Benlysta, LymphoStat-B | mab | human | BAFF | non-Hodgkin lymphoma etc. |
| Benralizumab | | mab | humanized | CD125 | asthma |
| Bertilimumab | | mab | human | CCL11 (eotaxin-1) | severe allergic disorders |
| Besilesomab | Scintimun | mab | mouse | CEA-related antigen | inflammatory lesions and metastases (detection) |
| Bevacizumab | Avastin | mab | humanized | VEGF-A | metastatic cancer, retinopathy of prematurity |
| Bezlotoxumab | | mab | human | *Clostridium difficile* | *Clostridium difficile* infection |
| Biciromab | FibriScint | Fab' | mouse | fibrin II, beta chain | thromboembolism (diagnosis) |
| Bimagrumab | | mab | human | ACVR2B | myostatin inhibitor |
| Bimekizumab | | mab | humanized | IL17A and IL17F | ? |
| Bivatuzumab mertansine | | mab | humanized | CD44 v6 | squamous cell carcinoma |
| Blinatumomab | | BiTE | mouse | CD19 | cancer |
| Blosozumab | | mab | humanized | SOST | osteoporosis |
| Bococizumab | | mab | humanized | neural apoptosis-regulated proteinase 1 | dyslipidemia |
| Brentuximab vedotin | | mab | chimeric | CD30 (TNFRSF8) | hematologic cancers |
| Briakinumab | | mab | human | IL-12, IL-23 | psoriasis, rheumatoid arthritis, inflammatory bowel diseases, multiple sclerosis |
| Brodalumab | | mab | human | IL-17 | inflammatory diseases |
| Brolucizumab | | mab | humanized | VEGFA | ? |
| Brontictuzumab | | mab | | Notch 1 | cancer |

TABLE 1-continued

| Name | Trade name | Type | Source | Target | Use |
|---|---|---|---|---|---|
| Canakinumab | Ilaris | mab | human | IL-1? | rheumatoid arthritis |
| Cantuzumab mertansine | | mab | humanized | mucin CanAg | colorectal cancer etc. |
| Cantuzumab ravtansine | | mab | humanized | MUC1 | cancers |
| Caplacizumab | | mab | humanized | VWF | thrombotic thrombocytopenic purpura, thrombosis |
| Capromab pendetide | Prostascint | mab | mouse | prostatic carcinoma cells | prostate cancer (detection) |
| Carlumab | | mab | human | MCP-1 | oncology/immune indications |
| Catumaxomab | Removab | 3funct | rat/mouse hybrid | EpCAM, CD3 | ovarian cancer, malignant ascites, gastric cancer |
| cBR96-doxorubicin immunoconjugate | | mab | humanized | Lewis-Y antigen | cancer |
| Cedelizumab | | mab | humanized | CD4 | prevention of organ transplant rejections, treatment of autoimmune diseases |
| Certolizumab pegol | Cimzia | Fab' | humanized | TNF-α | Crohn's disease |
| Cetuximab | Erbitux | mab | chimeric | EGFR | metastatic colorectal cancer and head and neck cancer |
| Ch.14.18 | | mab | chimeric | ??? | neuroblastoma |
| Citatuzumab bogatox | | Fab | humanized | EpCAM | ovarian cancer and other solid tumors |
| Cixutumumab | | mab | human | IGF-1 receptor | solid tumors |
| Clazakizumab | | mab | humanized | *Oryctolagus cuniculus* | rheumatoid arthritis |
| Cleneliximab | | mab | chimeric | CD4 | rheumatoid arthritis |
| Clivatuzumab tetraxetan | hPAM4-Cide | mab | humanized | MUC1 | pancreatic cancer |
| Codrituzumab | | mab | humanized | glypican 3 | cancer |
| Coltuximab ravtansine | | mab | chimeric | CD19 | cancer |
| Conatumumab | | mab | human | TRAIL-R2 | cancer |
| Concizumab | | mab | humanized | TFPI | bleeding |
| Crenezumab | | mab | humanized | 1-40-β-amyloid | Alzheimer's disease |
| CR6261 | | mab | human | Influenza A hemagglutinin | infectious disease/influenza A |
| Dacetuzumab | | mab | humanized | CD40 | hematologic cancers |
| Daclizumab | Zenapax | mab | humanized | CD25 (α chain of IL-2 receptor) | prevention of organ transplant rejections |
| Dalotuzumab[39] | | mab | humanized | insulin-like growth factor I receptor | cancer etc. |
| Dapirolizumab pegol | | mab | humanized | CD40 ligand | ? |
| Daratumumab | | mab | human | CD38 (cyclic ADP ribose hydrolase) | cancer |
| Dectrekumab | | mab | human | IL-13 | ? |
| Demcizumab | | mab | humanized | DLL4 | cancer |
| Denintuzumab mafodotin | | mab | humanized | CD19 | cancer |
| Denosumab | Prolia | mab | human | RANKL | osteoporosis, bone metastases etc. |
| Derlotuximab biotin | | mab | chimeric | histone complex | recurrent glioblastoma multiforme |
| Detumomab | | mab | mouse | B-lymphoma cell | lymphoma |
| Dinutuximab | | mab | chimeric | ganglioside GD2 | neuroblastoma |
| Diridavumab | | mab | human | hemagglutinin | influenza A |
| Dorlimomab aritox | | F(ab')₂ | mouse | ? | ? |
| Drozitumab | | mab | human | DR5 | cancer etc. |
| Duligotumab | | mab | human | HER3 | ? |
| Dupilumab | | mab | human | IL4 | atopic diseases |
| Durvalumab | | mab | human | CD274 | cancer |
| Dusigitumab | | mab | human | ILGF2 | cancer |
| Ecromeximab | | mab | chimeric | GD3 ganglioside | malignant melanoma |
| Eculizumab | Soliris | mab | humanized | C5 | paroxysmal nocturnal hemoglobinuria |
| Edobacomab | | mab | mouse | endotoxin | sepsis caused by Gram-negative bacteria |

TABLE 1-continued

| Name | Trade name | Type | Source | Target | Use |
|---|---|---|---|---|---|
| Edrecolomab | Panorex | mab | mouse | EpCAM | colorectal carcinoma |
| Efalizumab | Raptiva | mab | humanized | LFA-1 (CD11a) | psoriasis (blocks T-cell migration) |
| Efungumab | Mycograb | scFv | human | Hsp90 | invasive *Candida* infection |
| Eldelumab | | mab | human | interferon gamma-induced protein | Crohn's disease, ulcerative colitis |
| Elgemtumab | | mab | human | ERBB3 | cancer |
| Elotuzumab | | mab | humanized | SLAMF7 | multiple myeloma |
| Elsilimomab | | mab | mouse | IL-6 | ? |
| Emactuzumab | | mab | humanized | CSF1R | cancer |
| Emibetuzumab | | mab | humanized | HHGFR | cancer |
| Enavatuzumab | | mab | humanized | TWEAK receptor | cancer etc. |
| Enfortumab vedotin | | mab | human | AGS-22M6 | cancer expressing Nectin-4 |
| Enlimomab pegol | | mab | mouse | ICAM-1 (CD54) | ? |
| Enoblituzumab | | mab | humanized | B7-H3 | cancer |
| Enokizumab | | mab | humanized | IL9 | asthma |
| Enoticumab | | mab | human | DLL4 | ? |
| Ensituximab | | mab | chimeric | 5AC | cancer |
| Epitumomab cituxetan | | mab | mouse | episialin | ? |
| Epratuzumab | | mab | humanized | CD22 | cancer, SLE |
| Erlizumab | | F(ab')$_2$ | humanized | ITGB2 (CD18) | heart attack, stroke, traumatic shock |
| Ertumaxomab | Rexomun | 3funct | rat/mouse hybrid | HER2/neu, CD3 | breast cancer etc. |
| Etaracizumab | Abegrin | mab | humanized | integrin αvβ3 | melanoma, prostate cancer, ovarian cancer etc. |
| Etrolizumab | | mab | humanized | integrin α7 β7 | inflammatory bowel disease |
| Evinacumab | | mab | human | angiopoietin 3 | dyslipidemia |
| Evolocumab | | mab | human | PCSK9 | hypercholesterolemia |
| Exbivirumab | | mab | human | hepatitis B surface antigen | hepatitis B |
| Fanolesomab | NeutroSpec | mab | mouse | CD15 | appendicitis (diagnosis) |
| Faralimomab | | mab | mouse | interferon receptor | ? |
| Farletuzumab | | mab | humanized | folate receptor 1 | ovarian cancer |
| Fasinumab | | mab | human | HNGF | acute sciatic pain |
| FBTA05 | Lymphomun | 3funct | rat/mouse hybrid | CD20 | chronic lymphocytic leukaemia |
| Felvizumab | | mab | humanized | respiratory syncytial virus | respiratory syncytial virus infection |
| Fezakinumab | | mab | human | IL-22 | rheumatoid arthritis, psoriasis |
| Ficlatuzumab | | mab | humanized | HGF | cancer etc. |
| Figitumumab | | mab | human | IGF-1 receptor | adrenocortical carcinoma, non-small cell lung carcinoma etc. |
| Firivumab | | mab | human | influenza A virus hemagglutinin | ? |
| Flanvotumab | | mab | human | TYRP1(glycoprotein 75) | melanoma |
| Fletikumab | | mab | human | IL 20 | rheumatoid arthritis |
| Fontolizumab | HuZAF | mab | humanized | IFN-γ | Crohn's disease etc. |
| Foralumab | | mab | human | CD3 epsilon | ? |
| Foravirumab | | mab | human | rabies virus glycoprotein | rabies (prophylaxis) |
| Fresolimumab | | mab | human | TGF-β | idiopathic pulmonary fibrosis, focal segmental glomerulosclerosis, cancer |
| Fulranumab | | mab | human | NGF | pain |
| Futuximab | | mab | chimeric | EGFR | ? |
| Galiximab | | mab | chimeric | CD80 | B-cell lymphoma |
| Ganitumab | | mab | human | IGF-I | cancer |
| Gantenerumab | | mab | human | beta amyloid | Alzheimer's disease |
| Gavilimomab | | mab | mouse | CD147 (basigin) | graft versus host disease |
| Gemtuzumab ozogamicin | Mylotarg | mab | humanized | CD33 | acute myelogenous leukemia |
| Gevokizumab | | mab | humanized | IL-1β | diabetes etc. |
| Girentuximab | Rencarex | mab | chimeric | carbonic anhydrase 9 (CA-IX) | clear cell renal cell carcinoma[81] |

TABLE 1-continued

| Name | Trade name | Type | Source | Target | Use |
|---|---|---|---|---|---|
| Glembatumumab vedotin | | mab | human | GPNMB | melanoma, breast cancer |
| Golimumab | Simponi | mab | human | TNF-α | rheumatoid arthritis, psoriatic arthritis, ankylosing spondylitis |
| Gomiliximab | | mab | chimeric | CD23 (IgE receptor) | allergic asthma |
| Guselkumab | | mab | human | IL23 | psoriasis |
| Ibalizumab | | mab | humanized | CD4 | HIV infection |
| Ibritumomab tiuxetan | Zevalin | mab | mouse | CD20 | non-Hodgkin's lymphoma |
| Icrucumab | | mab | human | VEGFR-1 | cancer etc. |
| Idarucizumab | | mab | humanized | dabigatran | reversal of anticoagulant effects of dabigatran |
| Igovomab | Indimacis-125 | F(ab')$_2$ | mouse | CA-125 | ovarian cancer (diagnosis) |
| IMAB362 | | mab | human | CLDN18.2 | gastrointestinal adenocarcinomas and pancreatic tumor |
| Imalumab | | mab | human | MIF | cancer |
| Imciromab | Myoscint | mab | mouse | cardiac myosin | cardiac imaging |
| Imgatuzumab | | mab | humanized | EGFR | cancer |
| Inclacumab | | mab | human | selectin P | ? |
| Indatuximab ravtansine | | mab | chimeric | SDC1 | cancer |
| Indusatumab vedotin | | mab | human | GUCY2C | cancer |
| Infliximab | Remicade | mab | chimeric | TNF-α | rheumatoid arthritis, ankylosing spondylitis, psoriatic arthritis, psoriasis, Crohn's disease, ulcerative colitis |
| Intetumumab | | mab | human | CD51 | solid tumors (prostate cancer, melanoma) |
| Inolimomab | | mab | mouse | CD25 (α chain of IL-2 receptor) | graft versus host disease |
| Inotuzumab ozogamicin | | mab | humanized | CD22 | cancer |
| Ipilimumab | Yervoy | mab | human | CD152 | melanoma |
| Iratumumab | | mab | human | CD30 (TNFRSF8) | Hodgkin's lymphoma |
| Isatuximab | | mab | chimeric | CD38 | cancer |
| Itolizumab | | mab | humanized | CD6 | ? |
| Ixekizumab | | mab | humanized | IL-17A | autoimmune diseases |
| Keliximab | | mab | chimeric | CD4 | chronic asthma |
| Labetuzumab | CEA-Cide | mab | humanized | CEA | colorectal cancer |
| Lambrolizumab | | mab | humanized | PDCD1 | antineoplastic agent |
| Lampalizumab | | mab | humanized | CFD | ? |
| Lebrikizumab | | mab | humanized | IL-13 | asthma |
| Lemalesomab | | mab | mouse | NCA-90 (granulocyte antigen) | diagnostic agent |
| Lenzilumab | | mab | human | CSF2 | ? |
| Lerdelimumab | | mab | human | TGF beta 2 | reduction of scarring after glaucoma surgery |
| Lexatumumab | | mab | human | TRAIL-R2 | cancer |
| Libivirumab | | mab | human | hepatitis B surface antigen | hepatitis B |
| Lifastuzumab vedotin | | mab | humanized | phosphate-sodium co-transporter | cancer |
| Ligelizumab | | mab | humanized | IGHE | severe asthma and chronic spontaneous urticaria |
| Lilotomab satetraxetan | | mab | mouse | CD37 | cancer |
| Lintuzumab | | mab | humanized | CD33 | cancer |
| Lirilumab | | mab | human | KIR2D | ? |
| Lodelcizumab | | mab | humanized | PCSK9 | hypercholesterolemia |
| Lokivetmab | | mab | veterinary | Canis lupus familiaris IL31 | ? |
| Lorvotuzumab mertansine | | mab | humanized | CD56 | cancer |

TABLE 1-continued

| Name | Trade name | Type | Source | Target | Use |
|---|---|---|---|---|---|
| Lucatumumab | | mab | human | CD40 | multiple myeloma, non-Hodgkin's lymphoma, Hodgkin's lymphoma |
| Lulizumab pegol | | mab | humanized | CD28 | autoimmune diseases |
| Lumiliximab | | mab | chimeric | CD23 (IgE receptor) | chronic lymphocytic leukemia |
| Lumretuzumab | | mab | humanized | ERBB3 | cancer |
| Mapatumumab | | mab | human | TRAIL-R1 | cancer |
| Margetuximab | | mab | humanized | ch4D5 | cancer |
| Maslimomab | | ? | mouse | T-cell receptor | ? |
| Mavrilimumab | | mab | human | GMCSF receptor α-chain | rheumatoid arthritis |
| Matuzumab | | mab | humanized | EGFR | colorectal, lung and stomach cancer |
| Mepolizumab | Bosatria | mab | humanized | IL-5 | asthma and white blood cell diseases |
| Metelimumab | | mab | human | TGF beta 1 | systemic scleroderma |
| Milatuzumab | | mab | humanized | CD74 | multiple myeloma and other hematological malignancies |
| Minretumomab | | mab | mouse | TAG-72 | tumor detection (and therapy?) |
| Mirvetuximab soravtansine | | mab | chimeric | folate receptor alpha | cancer |
| Mitumomab | | mab | mouse | GD3 ganglioside | small cell lung carcinoma |
| Mogamulizumab | | mab | humanized | CCR4 | cancer |
| Morolimumab | | mab | human | Rhesus factor | ? |
| Motavizumab | Numax | mab | humanized | respiratory syncytial virus | respiratory syncytial virus (prevention) |
| Moxetumomab pasudotox | | mab | mouse | CD22 | cancer |
| Muromonab-CD3 | Orthoclone OKT3 | mab | mouse | CD3 | prevention of organ transplant rejections |
| Nacolomab tafenatox | | Fab | mouse | C242 antigen | colorectal cancer |
| Namilumab | | mab | human | CSF2 | ? |
| Naptumomab estafenatox | | Fab | mouse | 5T4 | non-small cell lung carcinoma, renal cell carcinoma |
| Narnatumab | | mab | human | RON | cancer |
| Natalizumab | Tysabri | mab | humanized | integrin α4 | multiple sclerosis, Crohn's disease |
| Nebacumab | | mab | human | endotoxin | sepsis |
| Necitumumab | | mab | human | EGFR | non-small cell lung carcinoma |
| Nemolizumab | | mab | humanized | IL31RA | ? |
| Nerelimomab | | mab | mouse | TNF-α | ? |
| Nesvacumab | | mab | human | angiopoietin 2 | cancer |
| Nimotuzumab | Theracim, Theraloc | mab | humanized | EGFR | squamous cell carcinoma, head and neck cancer, nasopharyngeal cancer, glioma |
| Nivolumab | | mab | human | PD-1 | cancer |
| Nofetumomab merpentan | Verluma | Fab | mouse | ? | cancer (diagnosis) |
| Obiltoxaximab | | mab | chimeric | *Bacillus anthracis* anthrax | *Bacillus anthracis* spores |
| Obinutuzumab | Gazyva | mab | humanized | CD20 | Chronic lymphatic leukemia |
| Ocaratuzumab | | mab | humanized | CD20 | cancer |
| Ocrelizumab | | mab | humanized | CD20 | rheumatoid arthritis, lupus erythematosus etc. |
| Odulimomab | | mab | mouse | LFA-1 (CD11a) | prevention of organ transplant rejections, immunological diseases |
| Ofatumumab | Arzerra | mab | human | CD20 | chronic lymphocytic leukemia etc. |
| Olaratumab | | mab | human | PDGF-R α | cancer |
| Olokizumab | | mab | humanized | IL6 | ? |
| Omalizumab | Xolair | mab | humanized | IgE Fc region | allergic asthma |

TABLE 1-continued

| Name | Trade name | Type | Source | Target | Use |
|---|---|---|---|---|---|
| Onartuzumab | | mab | humanized | human scatter factor receptor kinase | cancer |
| Ontuxizumab | | mab | chimeric/humanized | TEM1 | cancer |
| Opicinumab[1] | | mab | human | LINGO-1 | multiple sclerosis |
| Oportuzumab monatox | | scFv | humanized | EpCAM | cancer |
| Oregovomab | OvaRex | mab | mouse | CA-125 | ovarian cancer |
| Orticumab | | mab | human | oxLDL | ? |
| Otelixizumab | | mab | chimeric/humanized | CD3 | diabetes mellitus type 1 |
| Otlertuzumab | | mab | humanized | CD37 | cancer |
| Oxelumab | | mab | human | OX-40 | asthma |
| Ozanezumab | | mab | humanized | NOGO-A | ALS and multiple sclerosis |
| Ozoralizumab | | mab | humanized | TNF-α | inflammation |
| Pagibaximab | | mab | chimeric | lipoteichoic acid | sepsis (*Staphylococcus*) |
| Palivizumab | Synagis, Abbosynagis | mab | humanized | F protein of respiratory syncytial virus | respiratory syncytial virus (prevention) |
| Panitumumab | Vectibix | mab | human | EGFR | colorectal cancer |
| Pankomab | | mab | humanized | tumor specific glycosylation of MUC1 | ovarian cancer |
| Panobacumab | | mab | human | Pseudomonas aeruginosa | Pseudomonas aeruginosa infection |
| Parsatuzumab | | mab | human | EGFL7 | cancer |
| Pascolizumab | | mab | humanized | IL-4 | asthma |
| Pasotuxizumab | | mab | chimeric/humanized | folate hydrolase | cancer |
| Pateclizumab | | mab | humanized | LTA | TNF |
| Patritumab | | mab | human | HER3 | cancer |
| Pembrolizumab | | mab | humanized | PDCD1 | cancer etc. |
| Pemtumomab | Theragyn | ? | mouse | MUC1 | cancer |
| Perakizumab | | mab | humanized | IL17A | arthritis |
| Pertuzumab | Omnitarg | mab | humanized | HER2/neu | cancer |
| Pexelizumab | | scFv | humanized | C5 | reduction of side effects of cardiac surgery |
| Pidilizumab | | mab | humanized | PD-1 | cancer and infectious diseases |
| Pinatuzumab vedotin | | mab | humanized | CD22 | cancer |
| Pintumomab | | mab | mouse | adenocarcinoma antigen | adenocarcinoma (imaging) |
| Placulumab | | mab | human | human TNF | ? |
| Polatuzumab vedotin | | mab | humanized | CD79B | cancer |
| Ponezumab | | mab | humanized | human beta-amyloid | Alzheimer's disease |
| Priliximab | | mab | chimeric | CD4 | Crohn's disease, multiple sclerosis |
| Pritoxaximab | | mab | chimeric | *E. coli* shiga toxin type-1 | ? |
| Pritumumab | | mab | human | vimentin | brain cancer |
| PRO 140 | | ? | humanized | CCR5 | HIV infection |
| Quilizumab | | mab | humanized | IGHE | asthma |
| Racotumomab | | mab | mouse | N-glycolylneuraminic acid | cancer |
| Radretumab | | mab | human | fibronectin extra domain-B | cancer |
| Rafivirumab | | mab | human | rabies virus glycoprotein | rabies (prophylaxis) |
| Ralpancizumab | | mab | humanized | neural apoptosis-regulated proteinase 1 | dyslipidemia |
| Ramucirumab | Cyramza | mab | human | VEGFR2 | solid tumors |
| Ranibizumab | Lucentis | Fab | humanized | VEGF-A | macular degeneration (wet form) |
| Raxibacumab | | mab | human | anthrax toxin, protective antigen | anthrax (prophylaxis and treatment) |
| Refanezumab | | mab | humanized | myelin-associated glycoprotein | recovery of motor function after stroke |
| Regavirumab | | mab | human | cytomegalovirus glycoprotein B | cytomegalovirus infection |

TABLE 1-continued

| Name | Trade name | Type | Source | Target | Use |
|---|---|---|---|---|---|
| Reslizumab | | mab | humanized | IL-5 | inflammations of the airways, skin and gastrointestinal tract |
| Rilotumumab | | mab | human | HGF | solid tumors |
| Rinucumab | | mab | human | platelet-derived growth factor receptor beta | neovascular age-related macular degeneration |
| Rituximab | MabThera, Rituxan | mab | chimeric | CD20 | lymphomas, leukemias, some autoimmune disorders |
| Robatumumab | | mab | human | IGF-1 receptor | cancer |
| Roledumab | | mab | human | RHD | ? |
| Romosozumab | | mab | humanized | sclerostin | osteoporosis |
| Rontalizumab | | mab | humanized | IFN-α | systemic lupus erythematosus |
| Rovelizumab | LeukArrest | mab | humanized | CD11, CD18 | haemorrhagic shock etc. |
| Ruplizumab | Antova | mab | humanized | CD154 (CD40L) | rheumatic diseases |
| Sacituzumab govitecan | | mab | humanized | tumor-associated calcium signal transducer 2 | cancer |
| Samalizumab | | mab | humanized | CD200 | cancer |
| Sarilumab | | mab | human | IL6 | rheumatoid arthritis, ankylosing spondylitis |
| Satumomab pendetide | | mab | mouse | TAG-72 | cancer (diagnosis) |
| Secukinumab | | mab | human | IL-17A | uveitis, rheumatoid arthritis psoriasis |
| Seribantumab | | mab | human | ERBB3 | cancer |
| Setoxaximab | | mab | chimeric | E. coli shiga toxin type-2 | ? |
| Sevirumab | | ? | human | cytomegalovirus | cytomegalovirus infection |
| Sibrotuzumab | | mab | humanized | FAP | cancer |
| SGN-CD19A | | mab | humanized | CD19 | acute lymphoblastic leukemia and B-cell non-Hodgkin lymphoma |
| SGN-CD33A | | mab | humanized | CD33 | Acute myeloid leukemia |
| Sifalimumab | | mab | humanized | IFN-α | SLE, dermatomyositis, polymyositis |
| Siltuximab | | mab | chimeric | IL-6 | cancer |
| Simtuzumab | | mab | humanized | LOXL2 | fibrosis |
| Siplizumab | | mab | humanized | CD2 | psoriasis, graft-versus-host disease (prevention) |
| Sirukumab | | mab | human | IL-6 | rheumatoid arthritis |
| Sofituzumab vedotin | | mab | humanized | CA 125 | ovarian cancer |
| Solanezumab | | mab | humanized | beta amyloid | Alzheimer's disease |
| Solitomab | | mab | mouse | EpCAM | ? |
| Sonepcizumab | | ? | humanized | sphingosine-1-phosphate | choroidal and retinal neovascularization |
| Sontuzumab | | mab | humanized | episialin | ? |
| Stamulumab | | mab | human | myostatin | muscular dystrophy |
| Sulesomab | LeukoScan | Fab' | mouse | NCA-90 (granulocyte antigen) | osteomyelitis (imaging) |
| Suvizumab | | mab | humanized | HIV-1 | viral infections |
| Tabalumab | | mab | human | BAFF | B-cell cancers |
| Tacatuzumab tetraxetan | AFP-Cide | mab | humanized | alpha-fetoprotein | cancer |
| Tadocizumab | | Fab | humanized | integrin αIIbβ3 | percutaneous coronary intervention |
| Talizumab | | mab | humanized | IgE | allergic reaction |
| Tanezumab | | mab | humanized | NGF | pain |
| Taplitumomab paptox | | mab | mouse | CD19 | cancer[citation needed] |
| Tarextumab | | mab | human | Notch receptor | cancer |
| Tefibazumab | Aurexis | mab | humanized | clumping factor A | Staphylococcus aureus infection |
| Telimomab aritox | | Fab | mouse | ? | ? |
| Tenatumomab | | mab | mouse | tenascin C | cancer |
| Teneliximab | | mab | chimeric | CD40 | ? |

TABLE 1-continued

| Name | Trade name | Type | Source | Target | Use |
|---|---|---|---|---|---|
| Teplizumab | | mab | humanized | CD3 | diabetes mellitus type 1 |
| Teprotumumab | | mab | human | CD221 | hematologic tumors |
| Tesidolumab | | mab | human | C5 | ? |
| TGN1412 | | ? | humanized | CD28 | chronic lymphocytic leukemia, rheumatoid arthritis |
| Ticilimumab (=tremelimumab) | | mab | human | CTLA-4 | cancer |
| Tildrakizumab | | mab | humanized | IL23 | immunologically mediated inflammatory disorders |
| Tigatuzumab | | mab | humanized | TRAIL-R2 | cancer |
| TNX-650 | | ? | humanized | IL-13 | Hodgkin's lymphoma |
| Tocilizumab[6] (=atlizumab) | Actemra, RoActemra | mab | humanized | IL-6 receptor | rheumatoid arthritis |
| Toralizumab | | mab | humanized | CD154 (CD40L) | rheumatoid arthritis, lupus nephritis etc. |
| Tosatoxumab | | mab | human | *Staphylococcus aureus* | ? |
| Tositumomab | Bexxar | ? | mouse | CD20 | follicular lymphoma |
| Tovetumab | | mab | human | CD140a | cancer |
| Tralokinumab | | mab | human | IL-13 | asthma etc. |
| Trastuzumab | Herceptin | mab | humanized | HER2/neu | breast cancer |
| TRBS07 | Ektomab | 3funct | ? | GD2 | melanoma |
| Tregalizumab | | mab | humanized | CD4 | ? |
| Tremelimumab | | mab | human | CTLA-4 | cancer |
| Trevogrumab | | mab | human | growth differentiation factor 8 | muscle atrophy due to orthopedic disuse and sarcopenia |
| Tucotuzumab celmoleukin | | mab | humanized | EpCAM | cancer |
| Tuvirumab | | ? | human | hepatitis B virus | chronic hepatitis B |
| Ublituximab | | mab | chimeric | MS4A1 | cancer |
| Ulocuplumab | | mab | human | C—X—C chemokine receptor type 4 | hematologic malignancies |
| Urelumab | | mab | human | 4-1BB | cancer etc. |
| Urtoxazumab | | mab | humanized | *Escherichia coli* | diarrhoea caused by *E. coli* |
| Ustekinumab | Stelara | mab | human | IL-12, IL-23 | multiple sclerosis, psoriasis, psoriatic arthritis |
| Vandortuzumab vedotin | | mab | humanized | STEAP1 | cancer |
| Vantictumab | | mab | human | Frizzled receptor | cancer |
| Vanucizumab | | mab | humanized | angiopoietin 2 | cancer |
| Vapaliximab | | mab | chimeric | AOC3 (VAP-1) | ? |
| Varlilumab | | mab | human | CD27 | ? |
| Vatelizumab | | mab | humanized | ITGA2 | ? |
| Vedolizumab | | mab | humanized | integrin α4β7 | Crohn's disease, ulcerative colitis |
| Veltuzumab | | mab | humanized | CD20 | non-Hodgkin's lymphoma |
| Vepalimomab | | mab | mouse | AOC3 (VAP-1) | inflammation |
| Vesencumab | | mab | human | NRP1 | ? |
| Visilizumab | Nuvion | mab | humanized | CD3 | Crohn's disease, ulcerative colitis |
| Volociximab | | mab | chimeric | integrin α5β1 | solid tumors |
| Vorsetuzumab mafodotin | | mab | humanized | CD70 | cancer |
| Votumumab | HumaSPECT | mab | human | tumor antigen CTAA16.88 | colorectal tumors |
| Zalutumumab | HuMax-EGFr | mab | human | EGFR | squamous cell carcinoma of the head and neck |
| Zanolimumab | HuMax-CD4 | mab | human | CD4 | rheumatoid arthritis, psoriasis, T-cell lymphoma |
| Zatuximab | | mab | chimeric | HER1 | cancer |
| Ziralimumab | | mab | human | CD147 (basigin) | ? |
| Zolimomab aritox | | mab | mouse | CD5 | systemic lupus erythematosus, graft-versus-host disease |

In another embodiment, using photoacoustic or thermoacoustic technology, the circulating tumor, exosomes, or extracellular vesicles in the blood are quantified non-invasively by having a thermal energy source such as a laser, microwave, radio frequency (RF), or other unit mounted on the patient's wrist, neck, etc. and a receiver to count and record the sound wave generated by circulating cells to which the antibody-coated nanoparticles are attached.

In another embodiment, the ultrasonic receiver of the photoacoustic or thermoacoustic unit is an array of ultrasonic receivers mounted on a hand held probe. The hand held probe contacts the patient's skin via a gel placed over the area suspected to contain a tumor or lesion. It simultaneously records multiple photoacoustic signals from the lesion during thermal energy application. Thermal energy applied pulses can range from one per second to a hundred or thousand times or more per second. Each time a thermal pulse reaches the nanoparticles, the nanoparticles expand and create a photoacoustic response that is recorded by the photoacoustic receiver.

The Wnt signal pathway regulates cell-to-cell interactions and conveys the signals to the nucleus for cell differentiation and growth. Wnt genetic abnormality causes inflammation and cancer. The Wnt inhibitors, such as FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab prevent both cancer growth and inflammation however, the rock inhibitors and anti-integrins, such as Risuteganib, vedolizumab, and GSK inhibitors-3, or GSK 429286 reduce the inflammation and reduce cell proliferation.

Rho-associated protein kinase (Rock) is a kinase belonging to the family of serine-threonine Kinase involved in regulating the shape and the cytoskeleton of the cells, it is an important regulator of cell migration, stimulates PTEN phosphatase activity, leading to uncontrolled cell division in cancer. Rock is active in inflammatory processes, cancer, Parkinson's disease, diabetes, and many neurodegenerative diseases and production and stiffen collagen in tumors, such as pancreatic cancer. In one or more embodiments herein, Rock inhibitors are used to inhibit inflammatory processes, reduce TGF-β formation block cell migration, and inhibit metastatic spread of the tumors. There are a number of Rock inhibitors available however they have not been used in combination with functionalized nanoparticles to reduce the inflammation during immune therapy or thermoimmune therapy. The following compounds are readily available and some have been approved by the FDA: potent ROCK inhibitor; orally bioavailable Fasudil hydrochloride, inhibitor of cyclic nucleotide dependent- and Rho-kinases GSK 269962, potent and selective ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitorTC-57001, potent and highly selective ROCK inhibitor; orally active Y-27632 dihydrochloride.

In one embodiment, localized diagnostic and precision thermo-immune therapy is performed using electrical pulses and Low Intensity Focused Ultrasound (LIFU) or High intensity focused ultrasound (HIFU) applied to antibody coated pluralities of piezoelectric nanoparticles, such as coated carbon nanotubes (CNTs) grown on a silicon with zinc oxide (ZnO), coupled with an additional gold-coated CNT, chitosan, liposomes, liposomes filled with fluorescein or polymer micelles or nanoparticles usually poly(N-isopropylacrylamide) carrying a dye quenched with fluorescein, fluorescent dextrans or another dye or indicator that can be seen, and is able to be released when the nanoparticles are exposed to the LIFU or HIFU. The sound energy is converted to an electric signal that depolarizes the tumor cell membrane and makes it permeable to the medication/gene that is delivered thereto. The medication/genes are released by mechanical ultrasonic force with the potential heating of the polymeric coating of the nanoparticles carrying them.

In one embodiment, the antibody coated nanoparticles are conjugated with matrix metalloproteinase enzymes that when released by thermal energy activates hyaluronidase and which produces holes in the cell membrane permitting medications or genes along with CRISPR-cas9 to enter the cell cytoplasm.

In one embodiment, applying electrical pulses to the piezoelectric antibody piezoelectric nanoparticles convert the electricity to sound that can be recorded by multiple transducers located on the skin of the body providing information where the sound originating from inside the body and by triangulation of the sound signals converting them by using software executed by a processor to 2-3 D images of the tumor, etc. to which the piezoelectric nanoparticles are attached as electroacoustic images.

Figure 2:
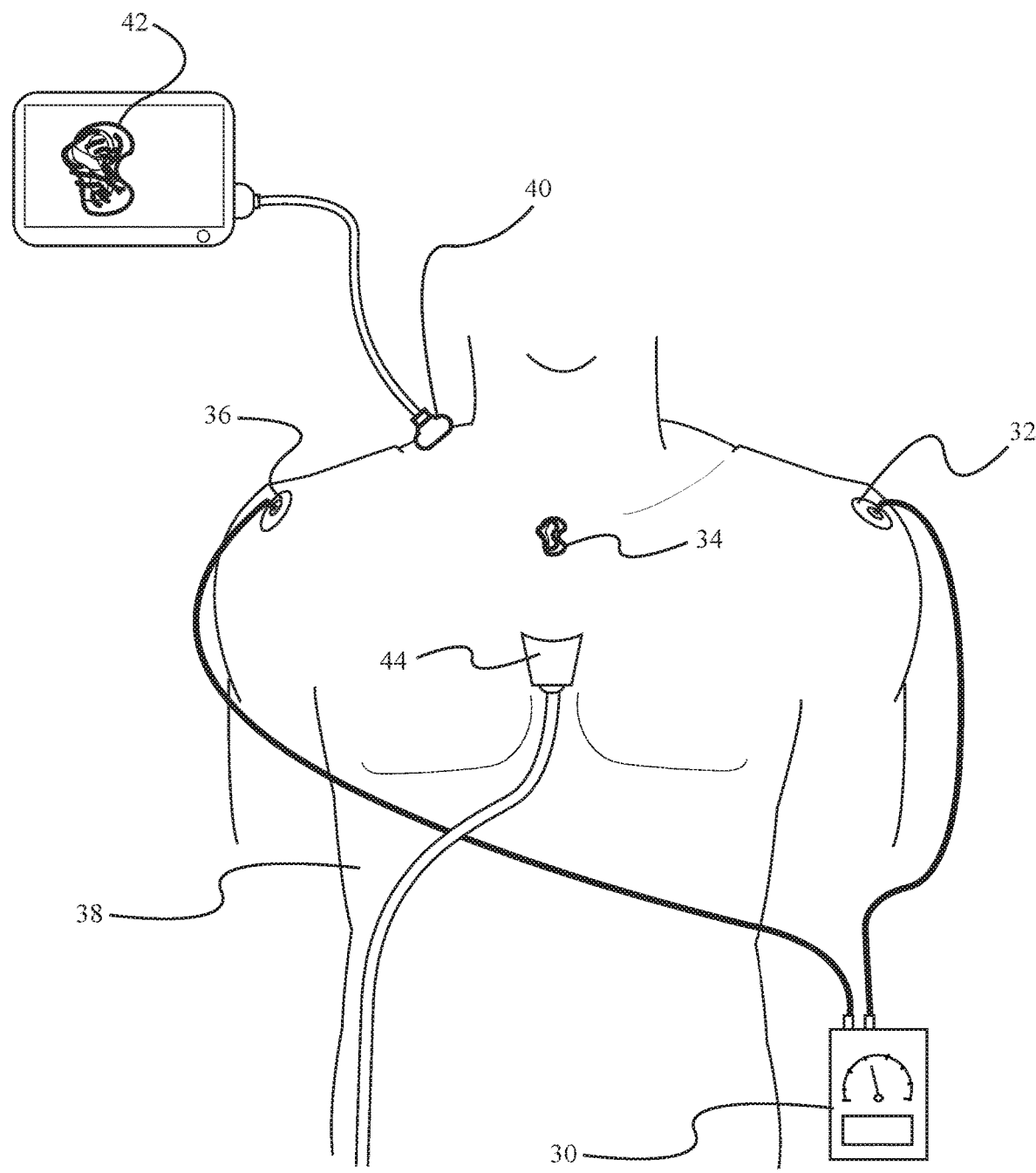
FIG. 2 illustrates a schematic diagram of a cancer treatment and imaging system, according to another embodiment of the invention.

In one embodiment, functionalized nanoparticles are exposed to electromagnetic radiation, microwaves, or radiofrequency radiation, or focused high power ultrasound 44 (see FIG. 2) in a thermal or non-thermal low power mode or non-focused ultrasound, or an alternating magnetic field and/or electrical current generated by a battery 30 (see FIG. 2) where low electrical current from a battery 30 passes from one side of the skin (i.e., the anode 32) through the body 38 and a lesion or tumor 34 to the cathode electrode 36 positioned on the opposite side of the skin on the body 38 to raise the temperature of the piezoelectric or pyroelectric nanoparticles that are injected inside the body 38 to be attached to the surface antigens of the normal cells or of the tumor cells and create a nanoparticle/tumor cell complex heated to 41-43 degrees C., and when exposed to pulses of electrical current generated by the battery 30 with an adjustable signal frequency and voltage, an acoustic response is produced by electrical stimulation of piezoelectric nanoparticles inside the body 38 that is called electroacoustic sounds or signals which can be captured with a transducer (e.g., ultrasound transducer 40 in FIG. 2), or microphone, converted to an electrical signal and is forwarded to a processor to be converted to a 1D, 2D, or 3D image 42 as an electroacoustic computed tomogram while the electrical pulse generated in the piezoelectric nanoparticles drives the medication, gene, in the tumor cells locally to damage the tumor cells by multiple modes of the therapy applied non-invasively under observation.

In one embodiment, the antibody coated pluralities of piezoelectric nanoparticles are conjugated with Wnt inhibitors and/or Rock inhibitors, such as selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitorTC-57001, potent and highly selective ROCK inhibitor; orally active Y-27632 dihydrochloride, and botulinum toxin Botox or GSK-3 inhibitors or anti-integrin, such as Risuteganib, vedolizumab, and GSK inhibitors-3, or GSK 429286 along with immune stimulators, such as pluralities of antibody coated viral-like particles, and toll like receptors TLR 2/ or 7/8 and 19 or IL 2 along with pluralities of antibody coated nanoparticles conjugated with checkpoint inhibitors such as the checkpoint inhibitor PD-1, or the Jagged 1 inhibitor 15D1 to be released by application of LIFU or HIFU from the nanoparticles.

In a further embodiment of the present invention, in the first compressive non-thermal mode, the focused ultrasonic wave generated by the ultrasound source has a frequency between about 10 kilohertz and about 500 kilohertz or more, and a 1 $W/cm^2$ to 10 $W/cm^2$ power that shakes up the nanoparticles and releases the medication from the polymeric coated piezoelectric nanoparticles.

In yet a further embodiment, the method further comprises the steps of (i) heating the nanoparticles in a second thermal mode using the focused ultrasound source at frequency of >1 MHz-50 MHz and a power of >5 $W/cm^2$ to 50 $W/cm^2$ or more that raises the temperature of the tumor cell/nanoparticle complex to a temperature of about 41° C. to about 43° C. that can be measured by the first harmonic waves or backscatter waves measured by multiple transducers indicating the temperature achieved, so as to damage one or more tumor cell membranes at the tumor site and melt the thermosensitive polymer coating of the nanoparticles, thereby releasing the fluorescein into the circulation of the patient and the medication and/or gene at the tumor site; and (ii) alternating the heating of the nanoparticles in the second thermal mode with the first compressive non-thermal LIFU mode under the control of a processor connected to both the imaging system and the focused ultrasound delivery system controlling the thermal energy intensity and duration of the ultrasound source.

In still a further embodiment, in the second thermal mode, the ultrasonic wave generated by the ultrasound source has a frequency between about 150 kilohertz and about 300 kilohertz, and a power of greater than 1 $W/cm^2$ to 50 $W/cm^2$.

In yet a further embodiment, the nanoparticles are coated with one or more antibodies, and the antibody coated nanoparticles contain medication and the medication is selected from the group consisting of Wnt inhibitors, such as Pimozide, Rock inhibitors, such as Fasudil, etc., metformin, buformin, syrosingopine, phenformin, anti-VEGFs, checkpoint inhibitors, or GSK-3 inhibitors or an anti-integrin, such as Risuteganib, vedolizumab, and GSK inhibitors-3, or GSK 429286, along with immune stimulators, such as pluralities of antibody coated viral-like particles (VLP), oncolytic viruses, and toll-like receptors TLR 2/ or 7/8 and 9 or IL 2 along with pluralities of antibody coated nanoparticles conjugated with checkpoint inhibitors, such as the checkpoint inhibitor PD-1, or Jagged 1 inhibitor 15D1 to be released by application of LIFU or HIFU from the nanoparticles or combinations thereof.

In one embodiment, piezoelectric nanoparticles are used to generate a sound wave from an electric pulse (e.g., generated by a battery) from the exposed nanoparticles, such as in a telephone receiver. Also, the piezoelectric nanoparticles may be exposed to an ultrasonic pulse which is absorbed by the piezoelectric nanoparticles, and the piezoelectric nanoparticles convert the sound wave into an electric pulse. In this embodiment, a tumor is imaged using an external electric pulse and antibody coated piezoelectric nanoparticles to create a sound wave inside the body to be imaged or by applying the external ultrasound to the antibody coated piezoelectric nanoparticles conjugated with a medication/gene or Wnt inhibitors, such as Pimozide or Rock inhibitors or GSK-3 inhibitors to inhibit TGF beta, or anti-integrin, such as Risuteganib, vedolizumab, and GSK inhibitors-3, or GSK 429286 along with immune stimulators, such as pluralities of antibody coated viral-like particles, and toll-like receptors TLR 2/ or 7/8 and 19 or IL 2 along with pluralities of antibody coated nanoparticles conjugated with checkpoint inhibitors, such as the checkpoint inhibitor PD-1, or the Jagged 1 inhibitor 15D1 and Anti-VEGFs to be released by application of LIFU or HIFU from the nanoparticles to treat a tumor non-invasively inside the body by depolarizing the tumor cell membrane by the generated electrons from the piezoelectric nanoparticles and making the cell membrane permeable to the medication (e.g., anti-cancer medication, etc.) by the internally generated electrical pulses.

In accordance with still one or more other embodiments of the present invention, there is provided a cancer treatment and imaging method comprising the steps of: (i) systemically administering intravenously or locally coated piezoelectric or pyroelectric nanoparticles or nanoshells, etc. to a patient in need thereof so as to target a tumor in the patient, the piezoelectric or pyroelectric nanoparticles being coated with a thermosensitive polymer, and a medication being conjugated with the thermosensitive polymer coating of the piezoelectric or pyroelectric nanoparticles, the piezoelectric or pyroelectric nanoparticles travel through the body attaching to surface antigens of tumor cells of the tumor so as to form tumor cell/nanoparticle complexes; (ii) applying a pulsed electrical current to the piezoelectric or pyroelectric nanoparticles using an electrical source at the site of the tumor so as to create an electroacoustic sound from the piezoelectric or pyroelectric nanoparticles; (iii) recording the electroacoustic sound generated by the piezoelectric or pyroelectric nanoparticles using a transducer to convert the electroacoustic sound to an electrical signal; and (iv) amplifying and transmitting the electrical signal to a processor so, as is done with an ultrasonic imaging system, that a 1-dimensional, 2-dimensional, or 3-dimensional image of the tumor structure is able to be generated from the piezoelectric nanoparticle/tumor cells to produce an electroacoustic computed tomogram.

In a further embodiment of the present invention, the method further comprises the step of (v) increasing the permeability of one or more tumor cell membranes of the tumor using the pulsed ultrasound, thereby initiating an electric pulse from the piezoelectric nanoparticles (e.g., quartz or perovskites) to depolarize the tumor cells attached to the nanoparticles, and minimally facilitating the entry of the medication/gene and or Wnt inhibitors FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab, or Rock inhibitors or GSK-3 inhibitors to inhibit TGF beta, or an anti-integrin, such as Risuteganib, vedolizumab, and GSK inhibitors-3, or GSK 429286, along with immune stimulators, such as pluralities of antibody coated viral-like particles, and toll like receptors TLR 2/ or 7/8 and 19 or IL 2 along with pluralities of antibody coated nanoparticles conjugated with checkpoint inhibitors, such as the checkpoint inhibitor PD-1, or Jagged 1 inhibitor 15D1 and Anti-VEGFs to be released by application of LIFU or HIFU from the nanoparticles into the depolarized tumor cells of the tumor.

In a further embodiment of the present invention, the method further comprises the step of (v) increasing the permeability of one or more tumor cell membranes of the tumor using the pulsed focused ultrasound, thereby initiating an electric pulse from the piezoelectric nanoparticles (e.g., quartz or perovskites or zinc oxide) conjugated with medication exposed to the ultrasound to depolarize the tumor cells, while increasing the temperature of the tissue with the focused ultrasonic waves and simultaneously measuring the tissue temperature with second harmonic wave back scattered ultrasound generated from the heated tissue recorded with a transducer, located on the patient's skin, connected to an imaging system, recording the tissue temperature. This imaging unit, is in turn connected via a processor with software executed thereby to the initial focused ultrasound producing unit, controlling the intensity of the pulsed ultrasound keeping it at <100 KHz intensity and at a power of <5 W/cm$^2$ to peel off and release medication from the nanoparticles (e.g., from antibody coated quartz or perovskites nanoparticles) conjugated with medication (similar to a commercially available ultrasonic watch or instrument cleaners that remove the dirt and cleaning the instrument) and to simultaneously depolarize the tumor cells attached to the piezoelectric nanoparticles, thus facilitating the entry of the medication/gene with CRISPR-cas9 into the depolarized tumor cells membrane.

In yet a further embodiment, the method further comprises the step of (v) heating the piezoelectric or pyroelectric nanoparticles using a ultrasound source operating in a thermal mode so as to raise the temperature of the tumor cell/nanoparticle complex controllably to a temperature of about 41° C. to about 43° C., thereby damaging one or more tumor cell membranes at the tumor site and melting the thermosensitive polymer coating of the nanoparticles to release the medication/gene or Wnt inhibitors, such as Pimozide or Rock inhibitors, such as Fasudil, etc., or GSK-3 inhibitors to inhibit TGF beta, or anti-integrin, such as Risuteganib, vedolizumab, and GSK inhibitors-3, or GSK 429286, along with immune stimulators, such as pluralities of antibody coated viral-like particles, and toll-like receptors TLR 2/ or 7/8 and 19 or IL 2 along with pluralities of antibody coated nanoparticles conjugated with checkpoint inhibitors, such as the checkpoint inhibitor PD-1, or Jagged 1 inhibitor 15D1 and Anti-VEGFs to be released by application of LIFU or HIFU from the nanoparticles at the tumor site.

In still a further embodiment, in a patient (e.g., a patient with a thyroid tumor), the electrical source comprises a battery device with an anode/cathode leads positioned on a first side of the body (neck) of the patient and a cathode being located on a second side of the neck of the patient, the pulsed electrical current passing through the neck of the patient from the anode to the cathode of the battery device, and where the pulsed electrical current passes through a tumor pretreated with intravenous or intra-arterial injection of the tumor supplying artery with antibody coated piezoelectric nanoparticles conjugated with medication attached to the tumor cell, where an electrical pulse creates an ultrasonic wave from the piezoelectric nanoparticles that can be recorded by an ultrasonic transducer located on the skin, imaged and localize the tumor precisely, then the lesion is treated non-invasively with a focused ultrasound beam through the skin and simultaneously heats up the tissue to the temperature of 39-40 degree C. to damage the tumor cells with thermal energy and depolarize the tumor cell membranes by converting the sound waves to an electric pulse to depolarize the tumor cells exposed to the ultrasound, making the cells permeable to the released medication/gene or Wnt inhibitors, Pimozide, FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab, etc. or Rock inhibitors, Fasudil, etc. or GSK-3 inhibitors to inhibit TGF beta, or anti-integrin such as Risuteganib, vedolizumab, and GSK-3, or GSK 429286, along with immune stimulators, such as pluralities of antibody coated viral-like particles, and toll-like receptors TLR 2/ or 7/8 and 19 or IL 2 along with pluralities of antibody coated polymeric nanoparticles, such as polylactic acid or polyglycolic acid conjugated with checkpoint inhibitors, such as the checkpoint inhibitor PD-1, Jagged 1 inhibitor 15D1 and Anti-VEGFs to be released by application of LIFU or HIFU from the nanoparticles.

Figure 3:
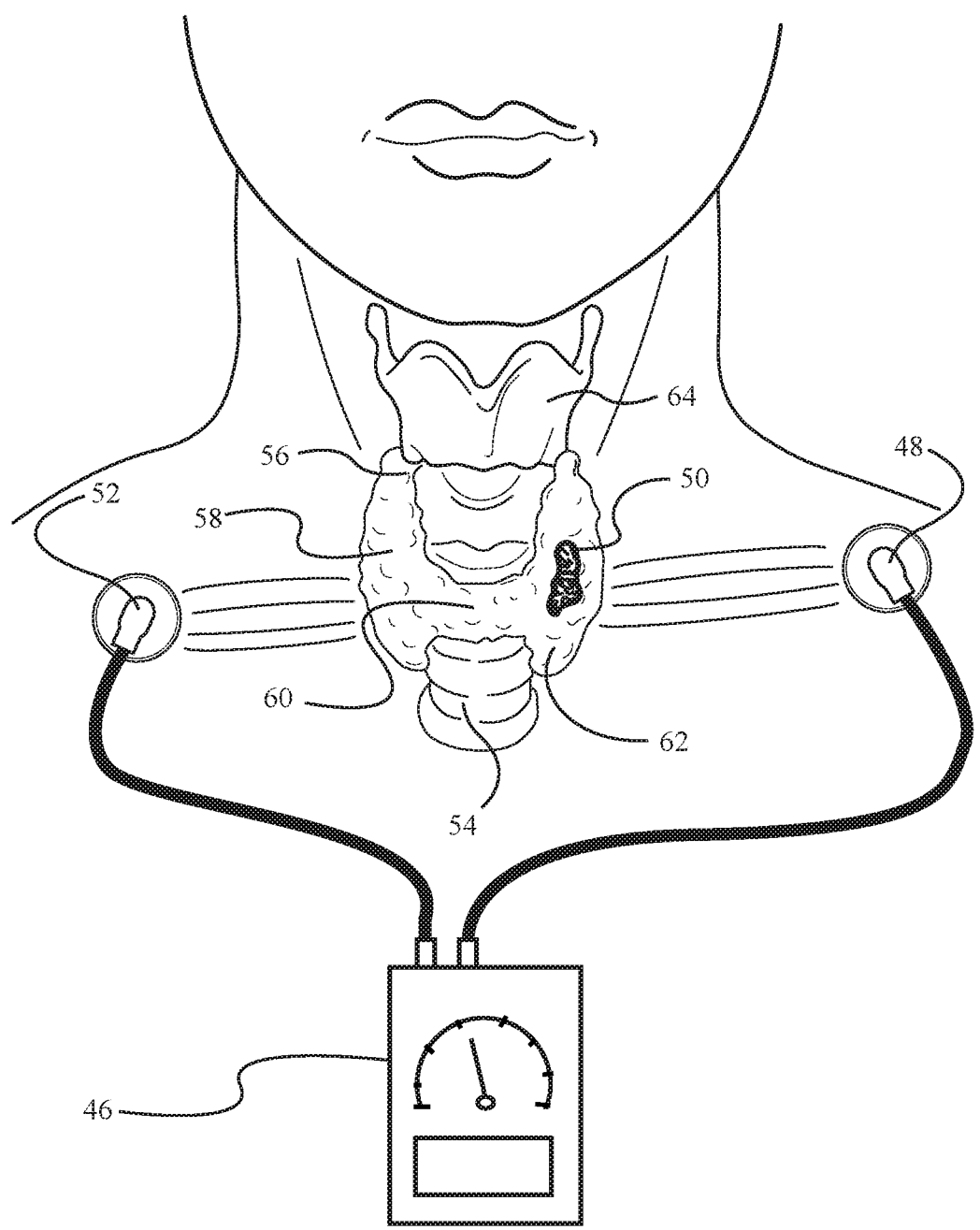
FIG. 3 illustrates a schematic diagram of a cancer treatment system, according to yet another embodiment of the invention, wherein a thyroid tumor is being treated.
Figure 4:
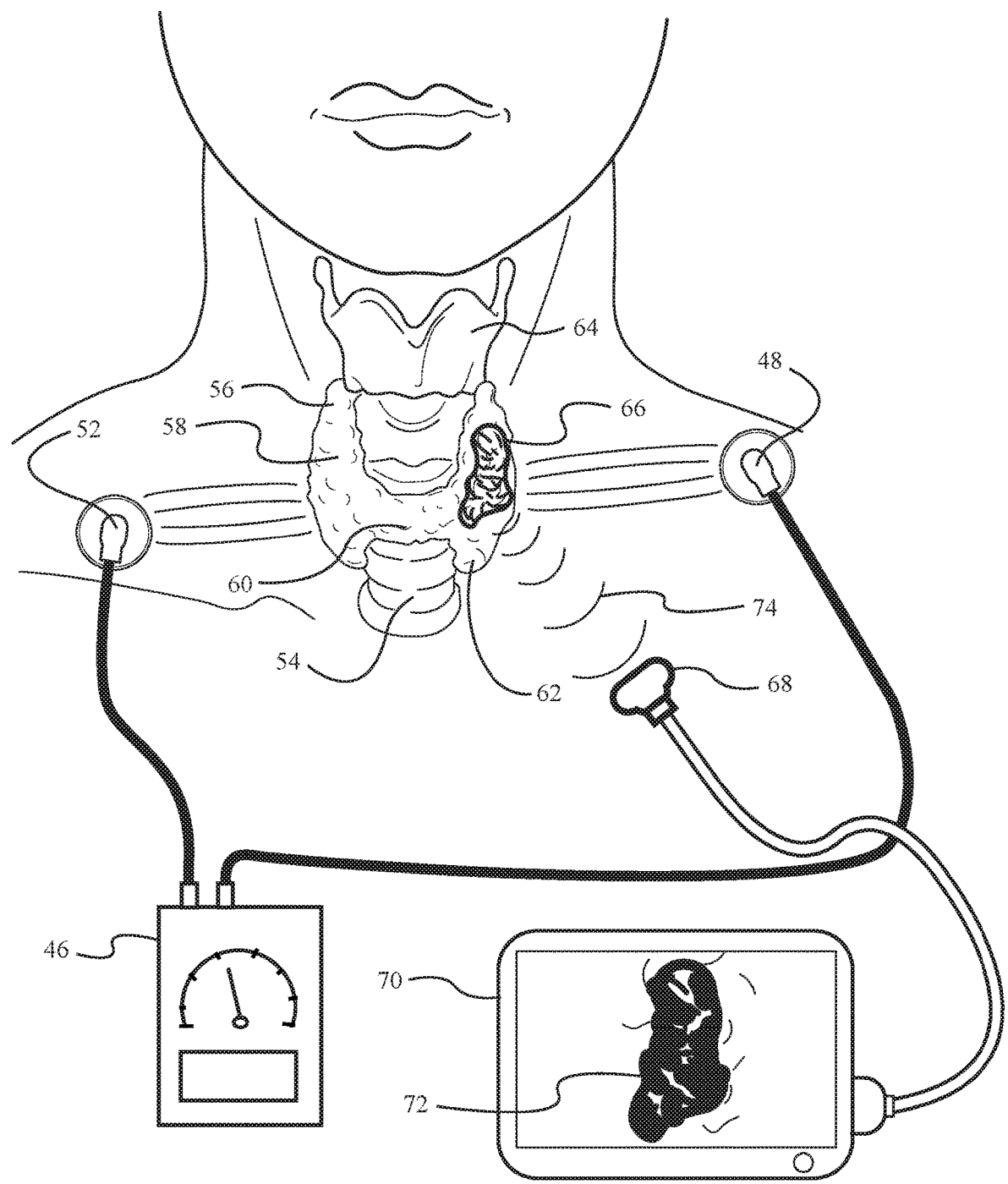
FIG. 4 illustrates a schematic diagram of a cancer treatment and imaging system, according to still another embodiment of the invention, wherein a thyroid tumor is being treated and imaged.
Figure 5:
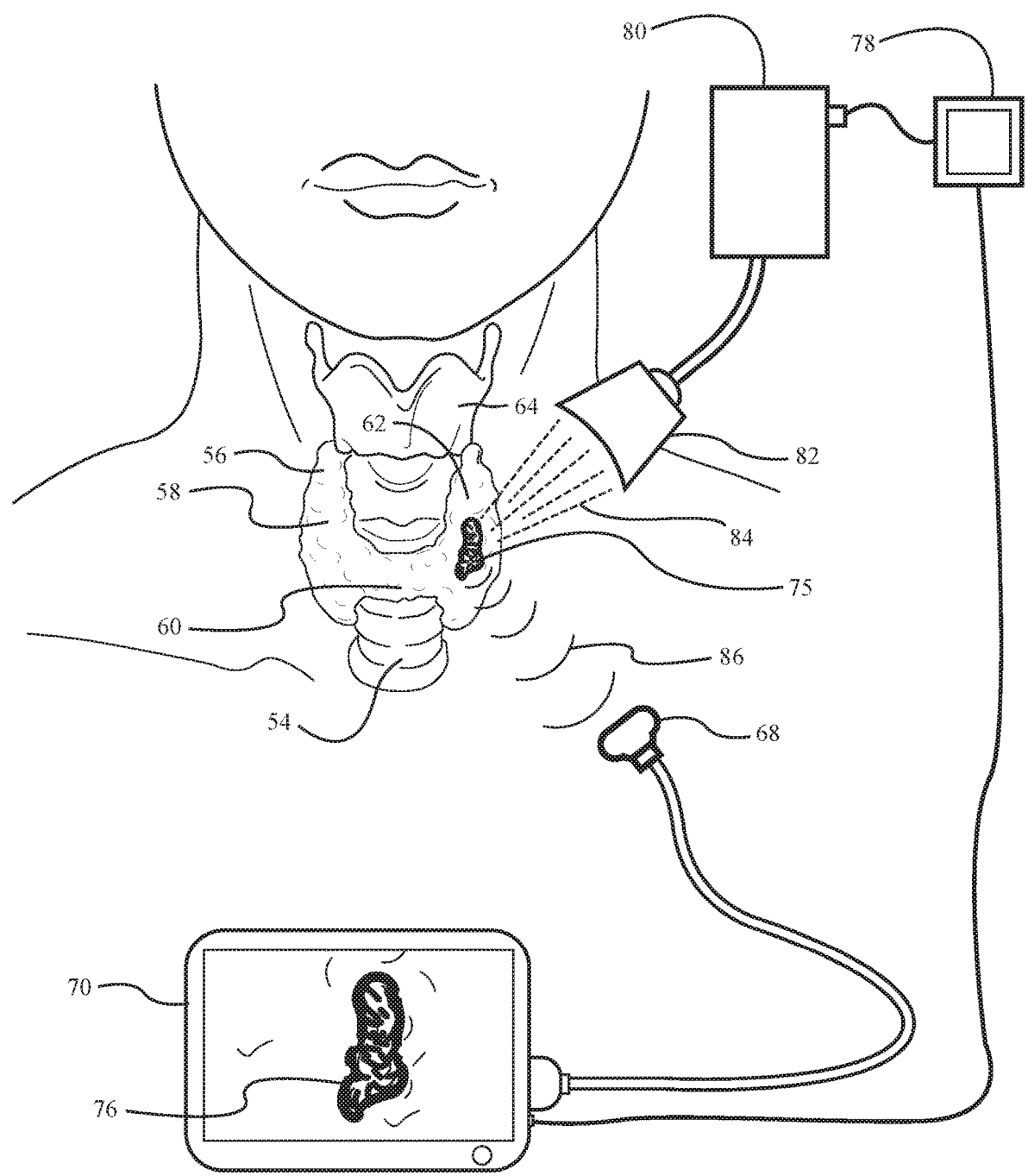
FIG. 5 illustrates a schematic diagram of a cancer treatment and imaging system, according to yet another embodiment of the invention, wherein a thyroid tumor is being treated and imaged.

In one or more embodiments, in a patient with a thyroid tumor 50 (see FIG. 3), an electrical source comprises a battery device 46 with an anode 48 being positioned on a first side of the body of the patient and a cathode 52 being located on a second side of the body of the patient, the pulsed electrical current (as diagrammatically indicated by the current lines in FIG. 3) passing through the body (e.g., the neck) of the patient from the anode 48 to the cathode 52 of the battery device 46, and where the pulsed electrical current passes through the tumor 50 which has been pretreated with antibody coated piezoelectric nanoparticles conjugated with medication, and attached to the tumor cells. In FIG. 3, it can be seen that the thyroid gland 56 of the patient, which is disposed around the trachea 54, comprises the right lobe 58, the left lobe 62, and the isthmus 60 connecting the right and left lobes 58, 62. Thyroid cartilage 64 is disposed above the thyroid gland 56 in FIG. 3. In FIG. 3, the battery device 46 is operatively coupled to a controller with software for generating the pulsed electrical current passing through the body of the patient between the anode 48 and the cathode 52. Turning to FIG. 4, it can be seen that the pulsed electrical current (as diagrammatically indicated by the current lines in FIG. 4) generated by the battery device 46 creates an ultrasonic wave 74 from the piezoelectric nanoparticles that can be recorded by an ultrasonic transducer 68 located on the skin. In FIG. 4, the ultrasonic transducer 68 is connected to a processor and monitor 70, which allows an image 72 of the thyroid tumor 66 in FIG. 4 to be reconstructed from the ultrasonic wave 74 received at the transducer 68. In addition, turning to FIG. 5, it can be seen that a thyroid tumor 75 may be treated non-invasively with a focused ultrasound beam 84 generated by an ultrasound array transducer 82. The focused ultrasound beam 84 passes through the skin and simultaneously heats up the tumor tissue and attached piezoelectric nanoparticles to a temperature of 39-40 degrees C. to damage the tumor cells of the tumor 75 with the thermal energy and to depolarize the tumor cell membranes by converting the sound waves to an electric pulse to depolarize the tumor cells exposed to the ultrasound, making the cells permeable to the medication/gene used to treat the tumor 75. In FIG. 5, it can be seen that the heating of the tumor 75 by the focused ultrasound beam 84 creates harmonic backscatter ultrasonic waves 86 from the piezoelectric nanoparticles that can be recorded by an ultrasonic transducer 68 located on the skin. In FIG. 5, similar to FIG. 4, the ultrasonic transducer 68 is connected to a processor and monitor 70, which allows an image 76 of the thyroid tumor 75 to be reconstructed from the harmonic backscatter ultrasonic waves 86 received at the transducer 68. In FIG. 5, the processor and monitor 70 connected to the transducer 68 are operatively coupled to another processor 78 that executes software for controlling the energy output of the focused ultrasound delivered by the ultrasound array transducer 82. That is, the processor 78 is operatively coupled to the ultrasound power source 80 so as to enable the energy output of the focused ultrasound delivered by ultrasound array transducer 82 to be selectively varied based upon feedback from the harmonic backscatter ultrasonic waves 86 received by the ultrasonic transducer 68. In this manner, in the system of FIG. 5, the temperature at the tumor site is able to be selectively controlled by varying the energy output of the focused ultrasound delivered by ultrasound array transducer 82. Also, in FIG. 5, when the focused ultrasound is applied to the tumor 75 with piezoelectric nanoparticles attached to the tumor 75, the ultrasound activates the piezoelectric nanoparticles to produce electrons to depolarize the tumor cells, and the focused ultrasound also creates second harmonic sound waves 86 that are recorded by the transducer 68 indicating the temperature at the tumor site. The imaging system 70 in FIG. 5 is connected to the processor 78 which, in turn, is connected to the ultrasound power source 80 so as to control the temperature of the tumor site at 41-43 degrees C. or more, as needed. In this manner, the tumor cells are depolarized and heated simultaneously (i.e., combining cell thermotherapy with cell depolarization) and medication conjugated with the piezoelectric nanoparticles is released at the tumor site so as to damage the tumor cells. Because the tumor cells have already been rendered generally defenseless by virtue of their depolarization, the medication is able to easily pass through the damaged tumor cell membranes, thus entering the cytoplasms of the damaged tumor cells and destroying the tumor cells.

In one embodiment, the antibody is obtained from the serum of the patient after the initial therapy to make a solution in combination with other adjuvants to sensitive the body to the potential recurrences of the tumor using genetic modification techniques, such as antibody coated nanoparticles conjugated with CRISPR-cas9 and siRNA or siDNA or RNA to modify the genetic components and prevent the tumor reoccurrences, along with antibody coated nanoparticles carrying Wnt inhibitors or Rock inhibitors or GSK-3 inhibitors to inhibit TGF beta, or an anti-integrin, such as Risuteganib, vedolizumab, and GSK inhibitors-3, or GSK 429286, along with immune stimulators, such as pluralities of antibody coated nanoparticles of polylactic acid or polyglycolic acid, viral-like particles, and toll-like receptors TLR 2/ or 7/8 and 19 or IL 2 along with pluralities of antibody coated polymeric nanoparticles, such as polylactic acid or polyglycolic acid conjugated with checkpoint inhibitors, such as the checkpoint inhibitor PD-1, Jagged 1 inhibitor 15D1, and Anti-VEGFs for slow release and long term effect and to be released by application of LIFU or HIFU from the nanoparticles.

In accordance with still one or more other embodiments of the present invention, there is provided a cancer treatment method using focused ultrasound comprising the steps of: (i) administering a plurality of piezoelectric or pyroelectric nanoparticles to a patient in need thereof so as to target a tumor in the patient, the administered piezoelectric or pyroelectric nanoparticles being coated with an antitumor antibody and a thermosensitive polymer, and the administered piezoelectric or pyroelectric nanoparticles containing medication, a gene, a checkpoint inhibitor, such as the checkpoint inhibitor PD-1, or Jagged 1 inhibitor 15D1, and/or viral-like particles (VLP), Allovectin-7, TLR 9 and quenched fluorescein in the thermosensitive polymer coating, at least some of the piezoelectric or pyroelectric nanoparticles attaching to surface antigens of tumor cells of the tumor so as to form a tumor cell/nanoparticle complex; and (ii) stimulating the piezoelectric or pyroelectric nanoparticles in a thermal or non-thermal mode using a ultrasound source that generates a focused ultrasonic wave so as to produce an electrical current from the piezoelectric or pyroelectric nanoparticles that paralyses cells of the tumor, thus permitting piezoelectric or pyroelectric nanoparticles with the antitumor antibody coating to enter the cytoplasms of the tumor cells and release the medication, gene, checkpoint inhibitor, and/or VLP, Allovectin-7 and Rock inhibitors or an anti-integrin, such as Risuteganib, vedolizumab, and GSK inhibitors-3, or GSK 429286 inside the tumor cells to prevent production of TGF beta and anti-VEGFs to combat anoxia and an anoxic induced factor and release the medication, gene, checkpoint inhibitor, such as the checkpoint inhibitor PD-1, or Jagged 1 inhibitor 15D1 and/or VLP, Allovectin-7, CD40 or TLR3, TLR7,9 from the thermosensitive polymer coating of the piezoelectric or pyroelectric nanoparticles upon the heating of the nanoparticles to a temperature of about 41° C. to about 43° C.

In a further embodiment of the present invention, the piezoelectric or pyroelectric nanoparticles are further conjugated with cell penetrating peptides (CPPs) or activatable cell-penetrating peptides (ACPPs) so to enhance cell penetration into the cells of the tumor prior to treatment to release the medication inside the tumor cells during non-thermal therapy with focused ultrasound at pulses or <1 MHz and power of <5 W/cm$^2$.

In yet a further embodiment, the nanoparticles are coated with one or more antibodies, and the antibody coated nanoparticles contain medication and the medication is selected from the group consisting of Wnt inhibitors, Pimozide, FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab, Rock inhibitors, such as Fasudil, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor; orally active Y-27632 dihydrochloride, and Botulinum toxin (Botox), etc., GSK inhibitors, metformin, buformin, syrosingopine, phenformin, anti-VEGFs, checkpoint inhibitors, such as the checkpoint inhibitor PD-1, Jagged 1 inhibitor 15D1, and combinations thereof further conjugated with cell penetrating peptides (CPPs) or activatable cell-penetrating peptides (ACPPs) so to enhance cell penetration into the cells of the tumor prior to treatment to release the medication inside the tumor cells during non-thermal therapy with focused ultrasound at pulses or <1 MHz and a power of <3 W/cm$^2$.

In one embodiment, a laser fiber optic can be used for diagnosis and therapy of the surface lesions after the injection of antibody coated nanoparticles for surface tumors or through the accessible cavities, eye, bladder mouth, throat, esophagus, stomach duodenum, rectum, colon, small intestinal tract and lung inserted through the natural orifices of the body, and intravenously or intra-arterially, locally in the skin surface or in the eye which is visible to bring the laser pulses to the tissue through which the blood vessels travel.

In one embodiment, the photoacoustic transducer probe can be moved in any direction (e.g., up and down, side to side, etc.) over the skin while recording the sound waves from the nanoparticles. Using a processor in the photoacoustic or thermoacoustic unit, one uses the photoacoustic or thermoacoustic response data to construct a two- or three-dimensional image of the tumor.

In one embodiment, the hand held probe permits scanning any bodily surface locally, including but not limited to breast, eye, CNS, spinal cord, extremities, internal organs, lung, nose, chest, trachea, throat, abdomen, and urogenital organs.

In one embodiment, the hand held probe permits scanning any bodily surface locally, including but not limited to breast, eye, CNS, spinal cord, extremities, internal organs, lung, nose, chest, trachea, throat, abdomen, and urogenital organs.

In one embodiment, a miniature capsule with an imaging camera, and equipped with a laser system, is swallowed by the patient. The capsule constantly radiates a laser pulse, as it passes through the intestinal tract and transmits recorded images to a receiver outside the body.

In one embodiment, a photoacoustic sound wave is produced when pluralities of antibody coated nanoparticles are administered intravenously that accumulate at the site of the tumors in the intestinal tract. The sound is recorded by a receiver located outside the body and in contact with body surface, such as the abdomen.

In one embodiment, as the capsule passes in front of a lesion in the intestinal tract that has accumulated the nanoparticles, it creates a photoacoustic sound that can be recorded by a receiver connected to the trunk of the patient and records the image of the lesion and the temperature at that site as the capsule travels through the intestine.

In one embodiment, the photoacoustic sound can be correlated with the video taken by the capsule and the location of the tumor is determined even if the tumor is too small to be recognized or too small to make any visible physical symptom. In one embodiment, the capsule emits a significant amount of energy to increase the temperature of the tumor site, and release the medication, gene, inhibitors, or GSK-3 inhibitors to inhibit TGF beta, or an anti-integrin, such as Risuteganib, vedolizumab, and GSK inhibitors-3, or GSK 429286, along with immune stimulators, such as pluralities of antibody coated nanoparticles of polylactic acid or polyglycolic acid, viral-like particles, and toll-like receptors TLR 2/ or 7/8 and 19 or IL 2 along with pluralities of antibody coated polymeric nanoparticles, such as polylactic acid or polyglycolic acid conjugated with checkpoint inhibitors, such as the checkpoint inhibitor PD-1, or Jagged 1 inhibitor 15D1 and Anti-VEGFs for slow release and long term effect and to be released by application of LIFU or HIFU to the antibody coated nanoparticles and damage and kill the tumor cells releasing their cellular antigens in the circulation to attract cellular immune response and kill the remaining tumor cells.

In one embodiment, a laser fiber optic with or without the camera, while pulsing laser energy, is passed through the mouth to the stomach or through the rectum into the colon or through the ureter inside the bladder, through the mouth, throat, trachea and bronchi, etc. or through the vagina inside the uterus or further through the fallopian tubes toward the ovaries.

In one embodiment, the laser pulse produces a photoacoustic or thermoacoustic response from the antibody coated nanoparticles attached to the tumor cells injected intravenously 1-2 minutes ahead permitting them to travel in the body and attach to the cells of a tumor that can be exposed to laser radiation to produce a photoacoustic sound and be recorded by a photoacoustic receiver located on the surface of the body which images the tumor while measuring the temperature generated at the tumor site by the laser to image the tumor in 2-D and 3-D format increasing the thermal radiation to increase the tumor temperature and kill the tumor cells at temperatures of 45-47 degrees C. while releasing Wnt inhibitors such as Pimozide, FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab and Rock inhibitors or GSK-3 inhibitors to inhibit TGF beta, or an anti-integrin, such as Risuteganib, vedolizumab, and GSK inhibitors-3, or GSK 429286, along with immune stimulators, such as pluralities of antibody coated nanoparticles of polylactic acid or polyglycolic acid, viral-like particles, and toll-like receptors TLR 2/ or 7/8 and 19 or IL 2 along with pluralities of antibody coated polymeric nanoparticles, such as polylactic acid or polyglycolic acid conjugated with checkpoint inhibitors, such as the checkpoint inhibitor PD-1, or Jagged 1 inhibitor 15D11 and Anti-VEGFs such as avastin or AYLEA or Pimozide that acts as an anti-angiogenic modulator through the inhibition of the AKT and VEGF signaling pathways, for slow release and long term effect and to be released by application of LIFU or HIFU from the nanoparticles.

In one embodiment, where a tumor is inaccessible through the natural orifices, a fiber optic endoscope is inserted through a small incision in the abdomen in the peritoneal cavity toward the liver, spleen, pancreas, or kidney for diagnostic or therapeutic purposes using the laser thermal energy, to recognize the location of the tumor by injecting the antibody-coated nanoparticles with the thermosensitive polymer conjugated with a medication and/or gene, shining the laser light over the suspected tumor area creates a photoacoustic sound which is imaged, heating preferentially the antibody coated pluralities of nanoparticles attached to the tumor cells damaging the cells at temperature of 31-43 degrees C. and releasing the conjugated medication, gene, toxins, Wnt inhibitors, such as Pimozide such as FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab, or Rock inhibitors, such as Fasudil, etc.

In one embodiment, other tumors inside the body can be accessed through insertion of a fiber optic through the blood vessels, arteries, or veins of an organ to induce a more organ specific diagnosis, and thermoimmune therapy, drug release or gene therapy without affecting the normal cells (e.g. in the brain, eye, extremities, or tumors localized in head and neck or urogenital organs).

In one embodiment, the laser fiber optic is inside a flexible tube through which antibody coated nanoparticles conjugated with a thermosensitive polymeric coating, such as PLA PGA, chitosan, polyanhydride, and carrying medication, siRNA, DNA, RNAi, CRISPR-cas9, Wnt inhibitors, or Rock inhibitors, or an anti-integrin, such as Risuteganib, vedolizumab, and GSK inhibitors-3, or GSK 429286, or CAR-t cells grown in cell culture and sensitized to the tumor antigen can be injected in the circulation or locally (e.g. inside an ocular melanoma, etc.).

In one embodiment, E-selectin binds to sialylated carbohydrates on the surface proteins of certain leucocytes. E-selectin ligands are expressed by neutrophils, monocytes, eosinophils, memory-effector T-like lymphocytes, and natural killer cells.

In one embodiment, the CAR-T cells or killer cells are grown in a tissue culture with antibody coated nanoparticles which are conjugated with e-selectin to attach to the surface of the CAR-T cells and ARE conjugated with VLP, Allovectin-7, administered initially after thermotherapy to attach to the tumor cells and enhance cellular immune response after thermotherapy.

In one embodiment, the CAR-T cells or killer cells are grown in a tissue culture with antibody coated nanoparticles to attach to the surface of the CAR-T cells and medications, toxins, enzymes, TNF, trail, or VLP, Allovectin-7, TLR 2, 7/8, 9 and oncolytic viruses that can be injected through a laser fiber optic tube slowly after thermotherapy of a localized tumor, or intermittently released to act like a repeated wave of solders attacking the tumor cells in the specific organ.

In one embodiment, the release of antibody coated pluralities of nanoparticles are observed under observation with an imaging system such as MRI, or ultrasound to verify the position of the tumor that is being treated with controlled thermotherapy using electromagnetic radiation, microwave, RF, or focused ultrasound or alternating magnetic field and the lesion is imaged by a photoacoustic or thermoacoustic imaging system and the temperature controlled.

In one embodiment, the laser fiber optic with the tube is inserted through the carotid artery to reach either sides of CNS harboring a tumor, such as glioblastoma.

In one embodiment, the laser fiber optic with the tube is inserted through the femoral artery and through the abdomen and moved toward any organ such as kidney, intestine, spleen, liver, or heart, or is inserted reach the carotid artery or any other part of the brain.

In one embodiment, the laser fiber optic with the tube is inserted through the femoral or radial artery to reach the tumor in the bone or extremities.

In one embodiment, the laser fiber optic with the tube is inserted through the radial arteries, to reach the lung or the heart.

In one embodiment, for example, to treat a brain tumor located in the right temporal lobe of the brain, the laser fiber/tube is inserted through the carotid artery and a drainage tube is placed in the jugular vein of the right side.

In one embodiment, to prevent a severe autoimmune response after tumor immunotherapy, one uses the return blood (e.g., from the jugular vein) for extracorporeal plasmapheresis, the nanoparticle assisted thermotherapy and imaging system are used to apply heavy thermal energy to a tube containing blood cells and to achieve a temperature as high as 60 degrees C. to kill the sensitized immune cells containing nanoparticles. Blood is then passed through a dielectrophoresis system to characterize and remove dead or live T-cells, sensitized killer cells, and tumor cells prior to re-infusing blood in the patient while simultaneously administering anti-inflammatory agents, including biologics. This reduces the severe autoimmune response often seen after tumor immunotherapy.

In one embodiment, the antibody coated nanoparticles conjugated with thermosensitive polymers such as PLA, PGA, chitosan, polyanhydride carrying medication, CRISPR-cas9 siRNS, DNA, RNAi, Wnt inhibitors, or Rock inhibitors can be injected in the circulation at a dose far below the systemically non-toxic dose so that the nanoparticles travel and attach to the tumor cells of the right temporal lobe of the brain.

In one embodiment, the magnetic or paramagnetic coated nanoparticles are heated either with laser light or from outside with a focused ultrasound in a compressive focused mode to strip the nanoparticle coating conjugated with a gene, medication or Wnt or Rock inhibitors, then the magnetic or paramagnetic coated nanoparticles are heated with the thermal mode of a focused ultrasound creating a thermal effect on the tumor while the degree of the temperature is imaged using a photoacoustic or thermoacoustic system where the receiver is attached to the surface of the skull, neck, or body or an MRI.

In one embodiment, the thermal energy is provided with either an alternating magnetic field or a microwave unit or RF unit or focused ultrasound.

In one embodiment, the tumor is heated to a temperature of 37-40 degrees C. and is maintained for 1-10 minutes as needed to damage the tumor cells.

In one embodiment, one uses the laser fiber optic/tube to induce a localized immunotherapy by administering antibody coated nanoparticles conjugated with a checkpoint inhibitor, and/or monoclonal antibody or aptamers or injected with a limited number of CAR-T cells to phagocytize the damaged tumor cells.

In one embodiment, the antibody coated nanoparticles are conjugated with viral-like particles (VLP) or Allovectin-7 oncolytic viruses and TLR 2 not only to damage the tumor cells, but also induce localized inflammation to attract the patient's lymphocytes, macrophages and killer cells to remove the dead tumor cells.

In one embodiment, the blood returning from the brain, etc. where the tumor is located is withdrawn through the jugular vein, passed through a dialysis or dielectrophoresis system to clean the blood from the dead cells and remove check inhibitors, VLP and toxins produced by the dead tumor cells to prevent a cytokine storm.

In one embodiment, after the thermoimmune therapy, Wnt inhibitors, FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab vantictumab (anti-FZD) and ipafricept (FZD8-Fc), or Rock inhibitors, GSK inhibitors, and anti-integrins, such as Risuteganib, vedolizumab, and GSK inhibitors-3, and/or anti-VEGF are administered to the tumor by conjugating them with antibody coated nanoparticles, to reach the tumor area and prevent excessive inflammation and edema.

In one embodiment, the tumor is located in the eye, nose, throat, or any part of the neck and head, mucosa, skin, tongue, throat, eye, esophagus, thyroid, salivary or lacrimal glands, nose, brain, legs, arms, etc. that can be reached through the natural body orifices, or through an artery or a vein.

In one embodiment, Wnt signaling is activated in many cancer stem cells and metastatic cells influencing the immune response to the cancer. Increased Wnt signaling releases a compound from the cancer cells by which the cancer cells evade recognition by the T-lymphocytes. Thus, increased Wnt signaling predicts a poor prognosis in cancer.

In one embodiment, the Wnt inhibitors are compounds, such as FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab, etc.

Glycogen Synthase Kinase-3 (GSK-3) is a serine/threonine protein kinase, which plays a key role in Wnt/β-catenin signaling during embryonic development, inflammation and cancer. Inhibition of GSK-3 inhibits Wnt pathway in cancer.

In one embodiment, the following compounds are readily available for conjugation with nanoparticles and some have been approved by the FDA: potent ROCK inhibitor; orally bioavailable Fasudil hydrochloride, inhibitor of cyclic nucleotide dependent- and Rho-kinases GSK 269962, potent and selective ROCK inhibitor GSK 429286, Selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitorTC-S7001, potent and highly selective ROCK inhibitor; orally active Y-27632 dihydrochloride, and Botulinum toxin (Botox).

In one embodiment, the data from the ultrasonic array probe of the photoacoustic or thermoacoustic unit is stored in a computer during the probe's motion, permitting video construction showing tumor shape, structure, location, etc. for video presentation, evaluation, and archiving.

In one embodiment, the unit is capable of storing vast quantities of data from photoacoustic signals (e.g., using infrared laser). The unit is also capable of storing vast quantities of data from non-stationary tissues, e.g., circulating tumor cells and exosomes in blood vessels, that have accumulated antibody coated nanoparticles on their cell membranes. The targeted cells can also be any normal or abnormal circulating cell in the blood or lymphatic system. The photoacoustic unit reproduces signals from these mobile cells and/or exosomes as photoacoustic cinematography/ angiography or video.

In one embodiment, the cinematography or video recording is done by the photoacoustic unit recording at least 30 frames/second of photoacoustic signals, and then converting them into an image of a moving object. A cinematography or video is performed by obtaining at least 30 frames of photos of a moving object per second. In photoacoustic videography or photoacoustic angiography, 30 or more frames of pulse signals from the heated nanoparticles per second are needed to reproduce or convert the still images to a moving object, e.g., blood flow, etc. by the unit. Use of such a system is known: Peyman et al. Ophthalmic Surg Laser Imaging 43 (2012) 143-51 doi: 10.3928.15428877-20120105-01 showing, however, lower resolution because no nanoparticles or photoacoustic imaging system was employed, and expressly incorporated by reference herein in its entirety.

In one embodiment, the photoacoustic processor converts the microscopic still images to a video or photoacoustic angiography; since the only moving parts in the vessels that are targeted with antibody coated nanoparticles are the circulating tumor cells or exosomes, extracellular vesicles or bubbles covered with antibody coated nanoparticles that are heated by a pulse of thermal energy produces an internal ultrasonic pulse signal recorded by the photoacoustic receiver. A moving image of the cells and exosomes can be created by the unit whether the cells are on the tumor interior or exterior.

Nanoparticle assisted photoacoustic video-angiography or nanoparticle assisted photoacoustic cinematography is novel and inventive. All "photoacoustic" terminology has previously been used for describing tissue heating or the difference in the temperature between two tissues, vessels vs. skin, and has been done with light alone, not in combination with nanoparticles. In one embodiment, the method is performed for therapy by providing the patient with at least one antibody-coated functionalized nanoparticle having a detectable property, with the antibody targeting the functionalized nanoparticle to a specific patient site, then heating the nanoparticles to generate a photoacoustic signal, i.e., thermal therapy, and imaging to visualize any localized nanoparticle at the site. The ultrasonic receiver of the photoacoustic unit is an array of ultrasonic receivers mounted on a hand held probe simultaneously recording multiple photoacoustic signals from the lesion during thermal energy application which in one embodiment is pulsating. The array of ultrasonic receivers of the photoacoustic unit mounted on a hand held probe simultaneously records multiple photoacoustic signals from the lesion or vessels during thermal energy application, reproducing motion of moving nanoparticles and/or cells as a nanoparticle assisted photoacoustic video-angiography or nanoparticle assisted photoacoustic cinematography.

In another embodiment, software associated with the photoacoustic unit can enhance either or both the photoacoustic signals and resulting images. Enhancement may facilitate differentiating exosomes from circulating cells due to the smaller exosome size. All exosomes or other types of extracellular vesicles are less than one micron; in contrast, tumor cells are five to twenty times larger than exosomes. The inventive system for the first time permits in vivo observation and separation of exosomes from tumor cells, and separation of circulating tumor cells from a tumor mass. The separated cells or cell structures can be observed, counted, and quantified to assess the therapeutic effect of a procedure on tumor cells.

In another embodiment, after imaging and therapy, the biomarkers are collected from liquid biopsies and compared with those obtained prior to therapy in different post-operative periods to confirm the therapeutic effect of the procedure and prognosticate the condition.

In another embodiment, the antibody coated nanoparticles are conjugated and administered with checkpoint inhibitors along with known immune therapy agents and vaccines to facilitate circulating killer cells attack and removal of tumor cells.

In one embodiment of the present invention, the thermosensitive polymer coating of the nanoparticles further comprises at least one rho-kinase inhibitor configured to be released when the thermosensitive polymer is melted, the rho-kinase inhibitor acting as an anti-inflammatory agent to prevent a cytokine storm resulting from the immunotherapy, and/or at least one Wnt inhibitor to inhibit Wnt activation in the cells of the tumor by FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab vantictumab (anti-FZD) and ipafricept (FZD8-Fc).

In one embodiment, an antibody/medication coated nanoparticle or nanoshell solution containing 2.67 nM gold nanorods, 2% human serum albumin, 0.04% (w/v) avidin is filled with PFC (C 3F 8) gas, then modified via biotin-avidin technique to result in anti VEGF (Avastin), aflibercept or Axitinib and quenched fluorescein, bubble liposomes carrying fluorescein which contain air pockets or nanoemulsions of PFC, gen or another dye or indicator, in the thermosensitive coating of the functionalized pluralities of nanoparticles with activatable cell-penetrating peptides (ACPPs) to target by ultrasonography the area of angiogenesis, such as tumor or suspicious breast cancer or ovarian cancer, while GNRs could induce photoacoustic or thermoacoustic imaging and thermal therapy under an alternating magnetic field (AMF) or a laser or focused ultrasound showing the theranostic value of this modality on keeping the temperature at the desired temperature of 41-43 degrees C. and 56 degrees C. so as not to damage the surrounding normal tissue, while treating a tumor (e.g., small intestinal tract lesions or mouth or skin tumors) at low temperature and release medication and Wnt inhibitors or Rock inhibitors, such as Fasudil (HA-1077 a selective RhoA/Rho kinase (ROCK) inhibitor), Y-27632, small molecule inhibitor of ROCK1 and ROCK2 which act as an anti-inflammatory agent and inhibit Wnt activation, from the thermosensitive nanoparticle under the control of the temperature to prevent excessive inflammatory response in the treated organ and the increased tumor biomarkers in the circulation after the thermotherapy has an important diagnostic (i.e., indicating presence of a tumor) and therapeutic value as biomarkers for the future management of the patient.

In one embodiment, Rock inhibitors, for example, Fasudil (HA-1077 a selective RhoA/Rho kinase (ROCK) inhibitor, or Y-27632, small molecule inhibitor of ROCK1 and ROCK2, etc. in liposomal preparation are administered systemically intravenously, intra-arterially locally, intra peritoneal, or in the cerebrospinal fluid with Biologic Response Modifiers using functionalized pluralities of nanoparticles with activatable cell-penetrating peptides (ACPPs) coated with Rock inhibitors, Wnt inhibitors, Temozolomide, Cetuximab in thermosensitive polymers to release the medication at the desired place at a desired time or combine them with standard anti-inflammatory agents, etc., such as steroids, aspirin or salicylic acid, Dexamethasone, NASIDs, etc. and deliver pluralities of nanoparticles (i.e., biodegradable or non-biodegradable nanoparticles) administered systemically intravenously, intra-arterially locally, intra peritoneal, or in the cerebrospinal fluid.

In one embodiment, Wnt inhibitors are compounds, such as FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab, etc.

In one embodiment, the thermosensitive polymer coating of the pluralities of antibody nanoparticles further comprises at least one rho-kinase inhibitor or Wnt inhibitors, GSK-3 inhibitors or anti-integrins and anti-mitotic medication such as taxane, Taxol, or paclitaxel, doxorubicin, etc. configured to be released when the thermosensitive polymer is melted, the rho-kinase inhibitor acting as an anti-inflammatory agent to prevent a cytokine storm resulting from the immunotherapy, and/or Wnt inhibitors are administered to inhibit Wnt activation in the cells of the tumor by FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab vantictumab (anti-FZD) and ipafricept (FZD8-Fc) to damage the potential tumor cells or metastatic cells or their exosomes and enhance mitotic cell death.

In another embodiment, polymeric nanoparticles or polysaccharide or synthetic polymers conjugated with biomarkers are administered to enhance a vaccination effect and are taken up by antigen presenting cells.

Any of the features or attributes of the above described embodiments and variations can be used in combination with any of the other features and attributes of the above described embodiments and variations as desired.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A cancer treatment and imaging method using compressive, non-thermal low power focused ultrasound, the method comprising the steps of:
   administering a plurality of nanoparticles, to a patient in need thereof so as to target a tumor in the patient, the administered nanoparticles being coated with an anti-tumor antibody, cell penetrating peptides (CPPs), and a polymer, and the administered nanoparticles containing a medication and/or gene, and a dye or indicator in the polymer coating, at least some of the nanoparticles attaching to surface antigens of tumor cells of the tumor so as to form a tumor cell/nanoparticle complex;
   exciting the nanoparticles in a first compressive, non-thermal, low power focused mode using an ultrasound source that generates a focused compressive ultrasonic wave so as to peel off the polymer coating of the nanoparticles by the focused vibrational force of the ultrasonic wave, thereby releasing the dye or indicator into the circulation of the patient and the medication and/or gene at the tumor site;
   imaging a body region of the patient using angiography so as to detect the dye or indicator released into the circulation of the patient;
   determining, by using a ultrasonic transducer, a temperature of tissue at the tumor site from a second harmonic of backscattered ultrasonic waves emanating from the tissue at the tumor site; and
   controlling, using a processor, an energy output of the ultrasound source based upon feedback from the backscattered ultrasonic waves received by the ultrasonic transducer.

2. The cancer treatment and imaging method according to claim 1, where, in the first compressive, non-thermal, low power focused mode, the ultrasonic wave generated by the ultrasound source has a frequency between 10 kilohertz and 100 kilohertz, and a power between 1 Watt per $cm^2$ and 10 Watts per $cm^2$.

3. The cancer treatment and imaging method according to claim 1, wherein the method further comprises the steps of:
   heating the nanoparticles in a second thermal mode using a high power focused ultrasound source that raises the temperature of the tumor cell/nanoparticle complex to a temperature between 41° C. and 43° C. so as to damage one or more tumor cell membranes at the tumor site and melt the polymer coating of the nanoparticles, thereby releasing the dye or indicator into the circulation of the patient and the medication and/or gene at the tumor site; and alternating the heating of the nanoparticles in the second thermal high power focused ultrasound mode with the focused compressive low power ultrasonic wave in the first compressive non-thermal mode with the focused ultrasound under the control of the processor controlling the thermal energy intensity and duration of the ultrasound source.

4. The cancer treatment and imaging method according to claim 3, where, in the second thermal mode, the ultrasonic wave generated by the ultrasound source has a frequency between 150 kilohertz and 1 megahertz, or greater than 1 megahertz, and a power of 1 Watt/cm$^2$ to 50 Watts/cm$^2$, or greater than 50 Watts/cm$^2$.

5. The cancer treatment and imaging method according to claim 3, where the nanoparticles comprise piezoelectric nanoparticles, and where the focused compressive ultrasonic wave in the first compressive non-thermal mode is delivered in a pulsed manner so as to generate an electric pulse from the piezoelectric nanoparticles that depolarizes the one or more tumor cell membranes so as to damage the tumor cells.

6. The cancer treatment and imaging method according to claim 1, where the nanoparticles contain the medication in the polymer coating, and the medication is selected from the group consisting of Wnt inhibitors, Rock inhibitors, metformin, buformin, syrosingopine, phenformin, anti-vascular endothelial growth factors (anti-VEGFs), checkpoint inhibitors, macrolides, glycogen synthase kinase (GSK) inhibitors, and combinations thereof.

7. The cancer treatment and imaging method according to claim 6, wherein the patient comprises exhausted cytotoxic lymphocytes in the microenvironment of the tumor, and the method further comprises the steps of:

administering at least one of Rock inhibitors, Wnt inhibitors, glycogen synthase kinase inhibitors, and anti-VEGFs to the microenvironment of the tumor in the patient;

removing toxins and dead cells from the blood of the patient after the administration of the at least one of the Rock inhibitors, Wnt inhibitors, glycogen synthase kinase inhibitors, and anti-VEGFs by electrophoresis or plasmapheresis so as to prevent a cytokine storm; and reinfusing the blood back into the patient after the blood has been cleaned by the electrophoresis or the plasmapheresis.

8. The cancer treatment and imaging method according to claim 1, wherein the dye or indicator released is fluorescein.

9. The cancer treatment and imaging method according to claim 1, where the nanoparticles comprise liposomes.

10. The cancer treatment and imaging method according to claim 1, wherein the nanoparticles further contain oncolytic viruses in the polymer coating; and wherein the exciting of the nanoparticles using the ultrasound source further releases the oncolytic viruses from the polymer coating, the oncolytic viruses preferentially infecting and killing the tumor cells of the tumor, the circulating tumor cells, and/or the tumor exosomes, and enhancing the cellular immune response.

11. The cancer treatment and imaging method according to claim 1, wherein the nanoparticles further contain an immune stimulator in the polymer coating, the immune stimulator being selected from the group consisting of bee venom, scorpion venom, viral-like particles (VLPs), IL-2, TLR 7, and combinations thereof; and wherein, when the immune stimulator is released from the polymer coating of the nanoparticles, the immune stimulator provides a signaling function for attracting T-cells and killer cells of the patient that attack the tumor cells of the tumor, the circulating tumor cells, and/or the tumor exosomes.

12. The cancer treatment and imaging method according to claim 1, wherein the nanoparticles contain the medication in the polymer coating, and the nanoparticles with the medication are administered by means of the nasal mucosa so as to travel through the olfactory nerves to the brain.

13. The cancer treatment and imaging method according to claim 12, further comprising the step of:

administering stem cells by means of the nasal mucosa so as to travel through the olfactory nerves to the brain.

* * * * *